United States Patent [19]
Skowron

[11] Patent Number: 6,107,020
[45] Date of Patent: Aug. 22, 2000

[54] MODEL FOR PROTECTIVE AND PATHOGENIC ROLES OF HIV-1 ENV-DIRECTED ANTIBODY DEPENDENT CELLULAR CYTOTOXICITY INTERACTION WITH VIRAL LOAD, AND USES THEREOF

[75] Inventor: Gail Skowron, West Greenwich, R.I.

[73] Assignee: Roger Williams Hospital, Providence, R.I.

[21] Appl. No.: 08/932,674

[22] Filed: Sep. 18, 1997

Related U.S. Application Data

[60] Provisional application No. 60/026,168, Sep. 20, 1996.

[51] Int. Cl.[7] .......................... C12Q 1/70; G01N 33/564; A01N 43/04; C07K 16/00
[52] U.S. Cl. ................... 435/5; 436/506; 514/44; 530/389.4; 530/389.6; 435/7.24; 435/29; 435/39; 435/810; 435/974
[58] Field of Search .................. 435/5, 7.24, 29, 435/39, 810, 974; 436/546; 514/44; 530/389.4, 389.6

[56] References Cited

PUBLICATIONS

Ellaurie, M. et al. (1990) "Human Immunodeficiency Virus (HIV) Circulating Immune Complexes in Infected Children" *AIDS Res. Hum. Retro.;* 6(12):1437–41.

Ho, D. (1996) "Viral Counts Count in HIV Infection" *Science;* 272:1124–25.

Kovacs, J.A. (1995) "Increases in CD4 T Lymphocytes with Intermittent Courses of IL–2 in Patients with Human Immunodeficiency Virus Infection" *N. Eng. J. Med.;* 332:567–575.

Levy, J. et al. (1994) "Passive Hyperimmune Plasma Therapy in the Treatment of Acquired Immunodeficiency Syndrome: Results of a 12–month Multicenter Double–Blind Controlled Trial" *Blood;* 84(7):2130–35.

Pennisi, E. et al. (1996) "Eradicating HIV From a Patient: Not Just a Dream?" *Science;* 272:1884.

Schechter, M.T. et al. (1990) "Susceptibility to AIDS Progression Appears Early in HIV Infection" *AIDS;* 4:185–90.

Skowron, G. (1994) "HIV–1 env–Specific Cellular Cytotoxicity in HIV–1–Seropositive Mothers and Their Infants" *AIDS Research and Human Retroviruses;* 10(Suppl. 2):S79–82.

*Primary Examiner*—Hankyel Park
*Attorney, Agent, or Firm*—Lahive & Cockfield, LLP; Giulio A. DeConti, Jr.,Esq.; Peter C. Lauro, Esq.

[57] ABSTRACT

Methods and kits for diagnosing the presence of and prognosing the of stages of HIV disease, involving correlating rate of CD4% decline, CMC activity and plasma HIV RNA load, are disclosed. In particular, the methods and kits pertain to diagnosis and prognosis of disease progression in retroviral infections.

19 Claims, 6 Drawing Sheets

MODEL FOR PROTECTIVE AND PATHOGENIC ROLES OF HIV-1 ENV-DIRECTED ANTIBODY DEPENDENT CELLULAR CYTOTOXICITY INTERACTION WITH VIRAL LOAD, AND USES THEREOF

RELATED APPLICATIONS

This application claims priority under 35 U.S.C. 119(e) to co-pending U.S. provisional application Ser. No. 60/026, 168, filed Sep. 20, 1996, the contents of which are hereby incorporated by reference.

GOVERNMENT FUNDING

Work described herein was supported in part by funding from the National Institutes of Health. The United States Government has certain rights in the invention.

BACKGROUND OF THE INVENTION

Despite the publication of studies of HIV patients correlating the presence of immune complexes with disease progression (Schechter M. T. et al., Susceptibility to AIDS Progression Appears Early in HIV Infection, *AIDS*, 1990; 4:185–90; and Ellaurie M., et al., Human Immunodeficiency Virus (HIV) Circulating Immune Complexes in Infected Children, *AIDS Res. Hum. Retro.*, 1990; 6(12):1437–41), the mechanism of immune complex-mediated CD4 depletion is not clearly understood. Depletion of CD4 cells is correlated with a negative outcome.

Antibody-dependent cellular cytotoxicity (ADCC) mediated by either monomeric IgG or immune complexes may also play a protective role in the HIV patient, by lysing infected cells. If the relative roles for ADCC in the control of viral load (protection) and CD4 cell decline (immunopathogenesis) are delineated, then strategies for intervention and modulation of these effects can be considered. The extent of natural antibodies to the CD4 binding site of gp120 is likely to influence the relative roles of protective versus pathogenic effects of ADCC. Definition of the time courses of protection and of pathogenesis will allow for rational testing of potential therapies. Cytokines such as interleukin-2 (IL-2), to enhance lysis of infected cells could be attempted during periods of low circulating levels of gp120 and low infected cell burden, as demonstrated by Kovacs J. A. et al., (Increases in CD4 T Lymphocytes With Intermittent Courses of IL-2 in Patients With Human Immunodeficiency Virus Infection, *N Eng J. Med.*, 1995; 332:567–575). In addition, for patients experiencing periods of high levels of circulating gp120, specific therapy with CD4 binding site antibodies, to bind free gp120 and prevent adsorption to uninfected CD4 cells, could be tested. Results of a placebo-controlled trial of passive therapy with hyperimmune plasma demonstrated a treatment benefit on CD4 cell count, supporting the potential use of such antibody therapy (Levy J. et al., Passive Hyperimmune Plasma Therapy in the Treatment of Acquired Immunodeficiency Syndrome: Results of a 12-month Multicenter Double-Blind Controlled Trial, *Blood*, 1994; 84(7):2130–35). Recent data on single dose studies of IL-12 in humans suggests that reses in both NK activity and in the number of cells bearing NK markers results from this intervention (Jacobson, M A et al., 1996, 3rd Conference on Retroviruses and Opportunistic Infections. Abstract 309). This would suggest similar cautions against the use of this cytokine in patients with high viral loads; in such patients, circulating gp120-coated uninfected and infected CD4 cells, which may not be lysed by NK cells in the absence of oxogenous stimulants, may be rapidly lysed during therapy with IL-12.

SUMMARY OF THE INVENTION

The invention comprises methods for quantitative evaluation of the causes of and potential therapies for CD4 depletion in retroviral disease, especially HIV. Currently no clinical or laboratory parameter can predict CD4% decline over time, perhaps with the exception of a documented nefdeletion. Data on a cohort of 21 patients demonstrated that quantitative assays of each of cell-mediated cytotoxicity (CMC) and HIV-specific RNA separately are important determinants of CD4 decline, but that neither is sufficient. An analysis of the interaction of these factors, based on the hypothesis that CMC activity is pathogenic only in the presence of sufficient viral load to produce free gp120 (antigen excess), the strength of the correlation is very high ($p=0.0003$, $r=-0.71$). A novel staging system is used to suggest types of therapeutic interventions most appropriate for a given patient.

The invention also comprises prognosis of progression of retroviral disease, with emphasis on progression of AIDS caused by HIV infection. A major aspect of the invention is to evaluate the relative contributions of each of free gp120, of antibody to gp120 and of effector cell characteristics to net CMC activity, in order to evaluate the importance of each component of CMC lysis and to assess possible therapeutic interventions to modulate in vivo antibody dependent cellular cytotoxicity, or ADCC. One aspect of the invention is the discovery that in HIV disease, CMC activity is dependent upon both humoral and cellular components of ADCC. Thus the invention features data obtained from in vitro assays of serum ADCC-mediating antibody, arming antibody, the number of natural killer (NK) cells and NK function in mediating killing of model target K562 cells. ADCC lysis and arming are used to provide insights into the relative importance of these components of CMC activity in determining the net effect of in vivo ADCC.

Furthermore, CD4 cell lysis mediated by ADCC was found also to be dependent on viral load, which serves as a surrogate marker for circulating, free gp120. A minimum viral load is necessary but not sufficient, since, even high levels of viral replication do not mediate CD4 cell depletion at low levels of NK function. The identification of specific characteristics in patients with extremes of CD4 maintenance or decline enables definition of rapid and slow CD4 decliner subgroups and suggests specific therapeutic interventions, aimed at modulating aspects of ADCC activity to decrease the rate of CD4 cell destruction. Thus a feature of the invention is a paradigm to correlate levels of free or immune complexed gp120, as measured by ELISA assay, with CMC activity and with viral load as measured by plasma RNA PCR. A preferred embodiment of the invention determines the dependence of CMC activity on levels of serum ADCC-mediating antibody, arming antibody, antibody to the CD4-binding site on gp120 and cell-surface binding antibodies.

Another aspect of the invention is to assess general measures of natural killer effector cell number ($CD3^-$/$CD16^+$,$56^+$) and function (lysis of K562 cells) and specific measures of ADCC and CMC effector function (effector ADCC, effector arming). A further feature of the invention is to investigate the mechanism of CMC lysis by modulating levels of gp120-specific immune complexes in vitro and assessing the ability of the resultant serum components to mediated ADCC, CMC and arming. Yet another feature of the invention is to describe the effects of initiating antiretroviral therapy on free and immune complexed gp120, serum ADCC and arming and NK effector cell number and function. An embodiment is to use these parameters to determine suitability of novel antiviral treatments, which can thus be customized for use at each stage of disease progression, which is determined by the criteria of the invention.

The invention features a method for diagnosing a stage of a retroviral infection in a subject with a retrovirus infection, comprising obtaining a biological sample from the subject, contacting the sample with target cells uninfected with the virus, these targets having been coated with a viral protein to determine CMC as a fraction of lysis of the target cells, and determination of retroviral load in the subject, in which the results of these determinations are used to diagnose a stage of a retroviral disease in the subject. Preferably the viral protein is an envelope protein and coats the target cells in vitro. In another aspect, the determinations of retroviral load and fraction of lysis of target cells are treated mathematically, and in a preferred embodiment, are multiplied or divided to obtain an index of the diagnosis. Preferably, the retroviral disease is selected from the group consisting of HIV-1, HIV-2, HTLV-1, HTLV-2, BIV, SIV, and FELV, most preferably, HIV-1 and HIV-2. Further, the method features determining cell mediated toxicity using CD4 cell targets, and preferably determining cell mediated toxicity by measuring antibody-dependent cellular-cytotoxicity lysis of gp120-adsorbed CEM.NK$^R$ targets by normal effector cells, which are supplied in vitro with serum from the HIV-1 infected patient.

Another aspect of the method involves determining retroviral load by assay of a viral coat gene product, in particular the gag gene product, which preferably is assayed by PCR analysis, and in the most preferred mode, by RNA PCR analysis.

Another aspect of the method features diagnosis of the stage of HIV disease progression according to one of four stages, in which classification of patients according to these stages enables superior customization of beneficial therapeutic regimens. The invention thus features a method for prognosis of response of a subject with a retroviral disease to treatment with a therapeutic agent, comprising obtaining a blood sample from the patient, treating the patient with the therapeutic agent, obtaining further blood samples from the patient during treatment, and subjecting cells of the blood samples to cell-mediated cytotoxicity assays, such that a decrease in cell-mediated cytotoxicity is a prognosticator for a therapeutic outcome. In addition, the invention features a method for delaying disease progression in a subject with an advanced stage of a retroviral disease, comprising administering to the subject at least one agent that binds to a viral gene product, to delay or inhibit the viral gene product capability of binding to uninfected cells and promoting cellmediated cytolysis, and monitoring the patient for reduction of cell-mediated cytolysis, thereby reducing progression of the retroviral disease.

These featured methods are applicable to the viral diseases associated with HIV-1, HIV-2, HTLV-1, HTLV-2, BIV, SIV, and FELV, and most preferably with HIV. The viral gene product which binds the CD4 cell in the case of HIV is gp1120, and similar receptor-docking proteins are found on the envelope of other retroviruses.

In another aspect, the invention features a kit for diagnosis and prognosis of a retroviral disease in a subject, comprising reagents for RNA PCR, reagents for cell-mediated cytotoxicity assay, apparatus for obtaining blood samples from said subject, a container, and instructions for use. Another kit is encompassed by the invention, for screening drugs suitable as chemotherapic agents to treat a subject with a retroviral disease, comprising reagents for RNA PCR, reagents for cell-mediated cytotoxicity assay, apparatus for obtaining serum samples from the subject, a container, and instructions for use of the reagents in conjunction with chemotherapeutic agents. Such a kit would be of use to customize a treatment regimen according to the particular stage of disease progression in a patient.

DETAILED DESCRIPTION OF THE INVENTION

I. Definitions

Figure 1A:
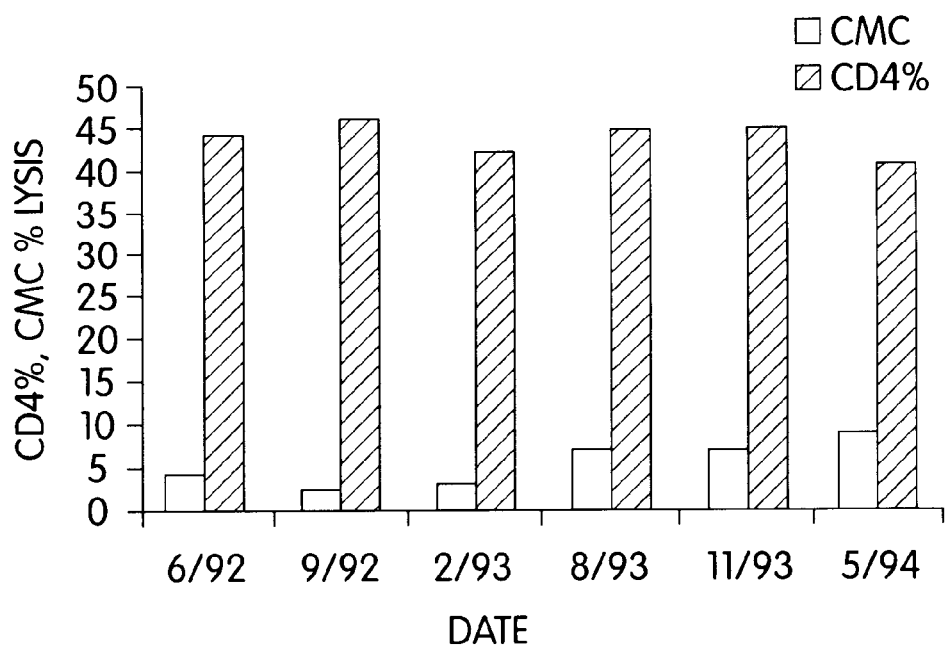
FIG. 1A is a bar graph showing cell-mediated cytotoxicity (CMC), expressed as percent lysis of target cells, and percent CD4 change per year, plotted by date of sampling in patient NM.

The term "subject," as used herein, refers to a living animal or human in need of diagnosis or prognosis for, or susceptible to, a condition, in particular a retroviral disease as defined below. In preferred embodiments, the subject is a mammal, including humans and non-human mammals such as apes, simians, dogs, cats, pigs, cows, sheep, goats, horses, rats, and mice. In the most preferred embodiment, the subject is a human. The term "subject" does not preclude individuals that are entirely normal with respect to tissue remodelling-associated conditions or normal in all respects. The subject may formerly have been treated surgically or by chemotherapy, and may be under treatment by hormone therapy or have been treated by hormone therapy in the past.

The term "patient," as used herein, refers to a human subject who has presented at a clinical setting with a particular symptom or symptoms suggesting one or more diagnoses with respect to retroviral disease. A patient may be in need of further categorization by clinical procedures well-known to medical practitioners of the art (or may have no further disease indications and appear to be in any or all respects normal). A patient's diagnosis may alter during the course of disease progression, such as development of further disease symptoms, or remission of the disease, either spontaneously or during the course of a therapeutic regimen or treatment. In the invention here, a patient described in the Examples is listed with other patients according to the most recent diagnosis of the medical condition, and any previous diagnoses, if different, are described in the text. Thus, the term "diagnosis" does not preclude different earlier or later diagnoses for any particular patient or subject or imply a stage of the disease. The term "prognosis" refers to assessment for a subject or patient of a probability of developing a condition or a stage associated with or otherwise indicated by assay of immunological parameters in a biological sample, preferably in urine.

The term "biological sample" includes biological samples obtained from a subject. Examples of such samples include urine, blood taken from a prick of the finger or other source such as intravenous, blood fractions such as serum and plasma, feces and fecal material and extracts, saliva, cerebrospinal fluid, amniotic fluid, mucus, and cell and tissue material such as cheek smear, Pap smear, fine needle aspiration, sternum puncture, lymph nodes, and any other biopsied material taken during standard medical and open surgical procedures. Preferably the sample is a blood sample.

The components of antibody-mediated cell cytotoxicity (ADCC) activity to be evaluated in patients are described by the following terms. The term "effector cell" means natural killer cell (NK), the number of which is determined by enumeration of the percentage of circulating lymphocytes bearing the $CD3^-/CD16^+, CD56^+$ phenotype counted by flow cytometry. NK cell lytic function is determined by lysis of the model target, K562 cells. Effector arming is the measurement of the ability of effector cells from patients with low CMC activity to be armed with sera from patients with high CMC activity and to mediate lysis of gp120-coated and HIV-infected targets. Effector ADCC is the measurement of the ability of effector cells from patients to mediate lysis of gp120-coated and HIV-infected targets in the indirect ADCC assay, using sera of known high ADCC activity.

Antibody activities are comprised of the following parameters. Indirect ADCC activity is the measurement of the ability of monomeric and immune-complexed antibody to mediate lysis of gp120-adsorbed, HIV-adsorbed or HIV-infected targets by normal effectors. CD4-binding site antibodies are a measurement of the ability of naturally occurring antibodies to block the site on gp120 at which CD4 binding is found. Cell surface binding antibodies shall mean the measurement of the amount of antibody which is specific for one or more species of cell surface expressed envelope antigens. Antigen immune complexes are, determined firstly, by serum arming, which is the measurement of the ability of sera to arm normal effectors and lyse gp120-coated or HIV-infected target cells and secondly, gp120/antibody immune complexes are measured by ELISA assay, utilizing antibody to gp120 and soluble CD4 to capture gp120, and detecting the complexes with a secondary antibody to gp120 or antibody to the Fc portion of IgG.

Samples to be studied are obtained from patients enrolled in the study, and have laboratory parameters measured at baseline and at months 4, 8, 16, 24, 32, and 40. Patients who initiate antiretroviral therapy during a prospective study have additional assays performed at early timepoints post-initiation of therapy (weeks 2, 4 and 8). These data are used to describe the effect of antiretroviral therapy on each measured parameter, in comparison to pretherapy values.

Correlative analyses are important in suggesting or proving that models based on in vitro measurements have clinical validity. Proof of causation requires use of an animal model, or manipulation of the in vivo situation to find predicted changes in immunologic or clinical outcome. Data show that: reduction in viral load affects CMC activity; further, a positive effect on disease progress has been found with infused antibody to the CD4-binding site on gp120. Purely virologic explanations for CD4 decline are inadequate, since in stage 4 patients, the higher virus load is not necessarily associated with CD4 decline.

The effect of ADCC is not masked by other mechanisms of CD4 decline. $CD8^+$ T cells are one mechanism by which infected $CD4^+$ T cells are cleared; it is much less likely that cytotoxic lymphocyte (CTL) lysis accounts for rapid CD4 decline, during which clearance of uninfected CD4 cells has been proposed. In addition, recent data (Y Riviere. et al., *AIDS Research and Human Retroviruses*, 1995; 11:903–907) suggest that the presence of gag-specific CTL activity is protective against the development of AIDS. In that study, env CTL activity (which may actually be measuring env ADCC in many patients), was not protective, and was further associated with disease progression, such as a greater rate of CD4 decline leading to a lower CD4 count and increased susceptibility to AIDS-defining infections.

By "rapid progressors", is meant that small percentage of AIDS patients which have shown less than 3 to 5 years from seroconversion to the development of AIDS, with rapid CD4 decline occurring a variable number of years after seroconversion. In clinical practice, initiation of treatment with antiretroviral medications may occur over a short, 1–2 year period of time, during which CD4 count changes rapidly. Hoover et al. from the (Multicenter AIDS Cohort Study (MACS)), documents median rates of absolute CD4 cell decline in slow and rapid progressor subgroups ranging from 124 to 189 cells per year in the 2.5 years that precede a CD4 count of 200. This is in contrast to the average fall of CD4 cell count (over the entire period of follow-up) in the local cohort of patients examined in subject invention, of approximately 50 cells per year and 68 cells per year in intermediate progressors at one site in the MACS cohort (C Rinaldo et al, *J Virology, 1995; 69:5838–5842*). Even in true rapid progressors with sharp falls in CD4 cell count (R. Connor et al., Increased viral burden and Cytopathicity Correlate Temporarrily With $CD4^+$ T-lymphocyte Decline and Clinical Progression in Human Immunodeficiency Virul Type 1-infected Individuals, *J. Virol.*, 1993; 67(4):1772–77), more gradual declines preceded and followed the rapid fall. The staging system of the instant invention includes stage 3 patients with very high rates of CD4% decline (with losses of between 4.8 and 13.5 percentage points per year). Finally, even in patients demonstrating a constant rate of CD4 cell decline throughout the course of disease, the proposed ADCC-mediated lysis of uninfected cells, which is a major feature of the invention remains a plausible contributing factor to this CD4 destruction.

Removal of excess in vivo gp120 as a therapeutic method follows directly from the model presented in instant application. Antiretroviral therapy that reduces viral load (and thus also reducing circulating levels of gp120), yields markedly reduced CMC activity, and CD4 cell counts rise as a consequence. A patient who received a single-dose infusion of antibody against the gp120 CD4 binding site demonstrated markedly reduced CMC activity. This antibody has so far been tested in single-dose studies only. The instant invention predicts that modulating the amount of free gp120, and/or altering the size or clearance of gp120 immune complexes affects rate of CD4 destruction. A further prediction is that the antibody need not neutralize virus to be effective in reducing the rate of CD4 destruction.

Figure 1B:
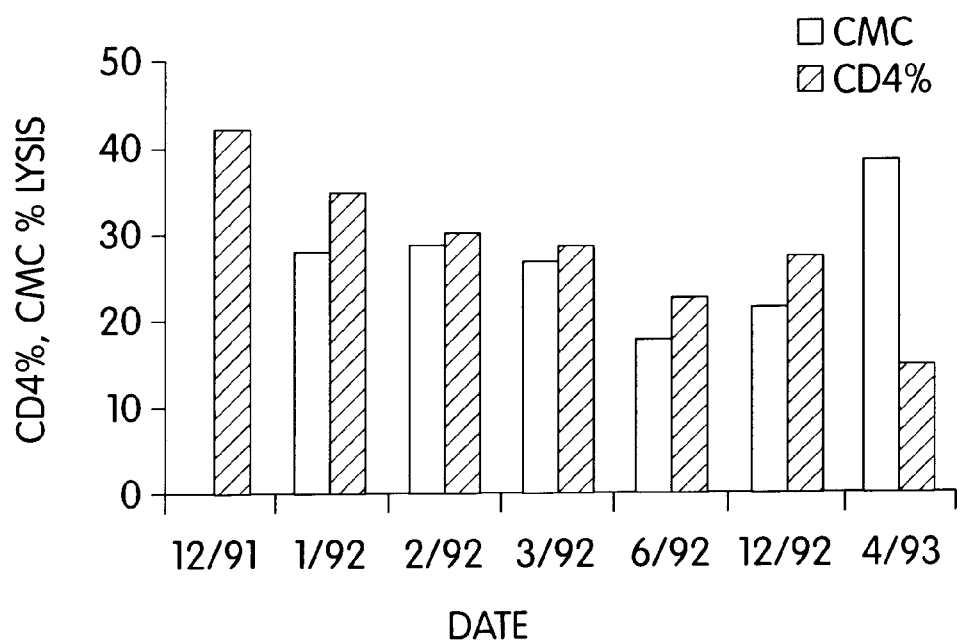
FIG. 1B is a bar graph showing cell-mediated cytotoxicity (CMC), expressed as percent lysis of target cells, and percent CD4 change per year, plotted by date of sampling in patient TPW.

By aggregate patient data in statistical analyses is meant to include mean values for CMC cytotoxicity, RNA PCR measurements, and CD4% decline per year calculated from linear regression analysis. For inclusion in analyses, data on patients must include at least 3 CMC and one or more RNA PCR assays, with at least one year of follow-up. FIGS. 1A and 1B, illustrate the reproducibility of the CMC assay over 2 years or more of patient observation. Additional data on serial CMC, arming and ADCC assays is found in Tables 5 and 7, to illustrating the reproducibility of repeated assays on the same set of patients over time. A rigorous statistical calculation of sample size is used to determine a sample size (N=60) necessary to confirm findings and allow detection of more subtle relationships between effector cell function and number, characteristics of gp120 antibodies and viral load.

Natural killer cells (NK) function activity changes with advancing immunodeficiency in HIV disease, as is seen in Examples below, in patients in stage 4 with low NK activity. The parameters of NK number and function are determinants of CMC activity as indicated by the presented data. Changes in NK subpopulations may occur due to HIV infection and progression of HIV disease (P-F Hu et al., *J AIDS*, 1995; 10:331–340). These changes are monitored by assays of ADCC effector cell activity and NK lysis of K562 cells.

Levels of observed circulating gp120 are sufficient to cause $CD4^+$ cells to become targets for NK cells. gp120, antibody and complement have been detected on the surface of circulating $CD4^+$ cells by flow cytometry (V. Daniel et al., Vox Sang, 1993; 64:31–36) and correlated with the rate of CD4 decline. Serum gp120 concentration is not a limiting factor in the adsorption of gp120 to $CD4^+$ cells; $CD4^+$ cells likely come in contact with gp120 in lymph nodes, where high levels of viral replication occur. The gp120 ELISA is used to detect gp120 production, and plasma RNA measurements are used to detect levels of HIV production.

Different levels of CMC and ADCC are observed among individuals with similar initial CD4 counts, however some of these patients demonstrate much more rapid disease progression than others. Longitudinal data on two long-term non-progressors (greater than 10 years since infection) show that one patient is in stage 1 (DEK), and the other is in stage 2 (JLG) The issue is no clearer with respect to CTLs: two recent papers from sites participating in the Multicenter AIDS Cohort Study (MACS) suggested that long-term non-progressors have either high (C Rinaldo et al., *J Virology*, 1995, 69:5838–5842) or low (J Ferbas et al., *J Infect Dis*, 1995; 172:329) CTL precursor frequencies against HIV proteins. Strong antiretroviral cellular immune responses can be either protective or pathogenic. The scientific and statistical rigor of the methods of the instant invention are applied to this determination.

The arming assay uses normal donor effectors, therefore this parameter alone is insufficient to explain changes in NK cell function over time. Stored serum samples are used in conjunction with prospective study design with longitudinal analysis (7 years or more). The arming assay provides important information relevant to CMC activity; however, additional data on a well characterized cohort, in which serial CMC assays are correlated with arming assays, to interpret arming data obtained using stored frozen sera.

The significance of the prognostic model and staging system lie in the potential clinical ability to slow CD4% decline during retroviral disease by modulating the components of CMC and viral load. Thus, targeted antiretroviral therapy, aimed at persons with significant CMC activity and viral load above a certain threshold (in stage 3) might be expected to result in a greater clinical benefit than therapy of persons with high viral load but low CMC activity (stage 4). An aspect of the invention is the prediction that IL-2 and IL-12 therapy to increase NK function is beneficial in stages 1 and 2 where viral load is low, and harmful in later stages the presence of high viral loads. Another outcome is the prediction that antibodies to CD4 binding site of gp120 are useful to reduce CMC in persons with free gp120 or viral load unresponsive to antiretroviral therapy. Thus measurement of serum gp120 defines groups of individuals for whom various therapies are useful or harmful.

Viral replicative differences affect both virus-mediated and gp120-mediated CD4 cell destruction. Measuring DNA-PCR, RNA PCR and serum gp120, identifies patients for whom further costly and time consuming virologic analysis is warranted. Long-term non-progressors are sampled for other parameters such as CTL responses. The invention utilizes these parameters, and correlates CMC (requiring fresh cells), arming, and ADCC (using both recently and remotely processed sera).

II. Cell-mediated and Antibody-mediated Mechanisms

A component of the model embodied by the instant invention is: ADCC activity directed against HIV-I infected cells in vivo, contributing to clearance of HIV-infected cells. This process may be protective at low viral burden (by limiting infected cell burden) or pathogenic at high viral burden (by lysing large numbers of infected CD4 cells) and in the presence of sufficient free gp120, lysing gp120-coated, uninfected CD4 cells, leading to rapid CD4 decline. During the course of HIV infection, the relative contribution of each of these effects is governed by infected cell burden, viral load, the amount of circulating gp120 available to bind to uninfected CD4 cells, the presence of ADCC-mediating antibody and the ability of natural killer cells to mediate ADCC.

CD4 cell depletion is a hallmark of progressive HIV disease, leading to immunodeficiency and opportunistic infection (Centers for Disease Control and Prevention. Pneumocystis pneumonia-Los Angeles. Mortal. Morbid. Weekly Report. 1981; 30:250–2; Centers for Disease Control and Prevention. Kaposi's sarcoma and Pneumocystis pneumonia among homosexual men-New York City and California. Mortal. Morbid. Weekly Report. 1981; 30:305–8; and Pantaleo et al., The Immunopathogenesis of Human Immunodeficiency Virus Infection. *N Engl. J Med.*, 1993; 328:327–335). The mechanism of CD4 loss is not understood; however, many theories have been proposed, such as viral cytopathic effects (Garry R. F., Potential Mechanisms for the Cytopathic Properties of HIV, *AIDS*, 1989; 3:683–694; and Lifson J. D. et al., AIDS Retrovirus Induced Cytopathology: Giant Cell Formation and Involvement of CD4 Antigen, *Science*, 1986; 232:1123–1127), immune destruction through superantigen effects (Imberti L. et al., Selective Depletion in HIV Infection of T Cells That Bear Specific T Cell Receptor $V_\beta$ Sequences, *Science*, 1991; 254:860–862; and Pantaleo G. et al., Perturbation of the T Cell Receptor $V_\beta$ Repertoire in Peripheral Blood T Cells of HIV Infected Individuals, *Clin. Res.*, 1992; 40:253A, Abstract), and programmed cell death (Terai C. et al., Apoptosis as a Mechanism of Cell Death in Cultured T Lymphoblasts Acutely Infected With HIV-1, *J. Clin. Invest.*, 1991; 87:1710–1715). An effective immune response may have pathogenic as well as beneficial effects. In HIV infection, the major cells infected with HIV are lymphocytes and macrophages, and thus clearance of virus-infected cells leads to destruction of immunologically important cells.

Two major mechanisms of cell-mediated immunity to HIV are cytotoxic T cells (CTLs) and antibody-dependent cellular cytotoxicity (ADCC). CTL lysis is mediated by CD8$^+$ or CD4$^+$ lymphocytes and is directed at processed viral antigens which have been expressed on the surface of the infected cell, and have become associated with MHC class I or class II molecules (Walker B. D. et al., HIV-specific Cytotoxic T Lymphocytes in Seropositive Individuals, *Nature*, 1987; 328:345–348; Plata F. et al., AIDS Virus-specific Cytotoxic T Lymphocytes in Lung Disorders, *Nature*, 1987; 328:348–351; and Siliciano R. F. et al., Analysis of Host-virus Interactions in AIDS With Anti-gp120 T Cell Clones: Effect of HIV Sequence Variation and a Mechanism for CD4$^+$ Cell Depletion, *Cell*, 1988; 54:561–575). ADCC is mediated by natural killer (NK) cells, through Fc receptor (FcR) binding of specific antiviral antibodies (Clark R. A. et al., Studies on the Mechanism of Antibody-dependant Polymorphonuclear Leukocyte-mediated Cytotoxicity, *J. Immunol.*, 1977; 119:1413–1418; Sissons J. et al., Killing of Virus Infected Cells by Cytotoxic Lymphocytes, *J. Infect Dis.*, 1980; 142:114–119; and Trinchieri G., Biology of Natural Killer Cells. In: Advances in Immunology, *Academic Press*, 1989; 47:187–376).

An important distinction between CTL and ADCC is that in ADCC, lysis of target cells ADCC does not require MHC matching, and the viral antigen need not be endogenously produced or processed (Rook A. H. et al., Sera From HTLV-III/LAV Antibody-positive Individuals Mediate Antibody-Dependent Cellular Cytotoxicity Against HTLV-III/LAV-Infected T Cells, *J. Immunol.*, 1987; 138:1064–1067; Ljunggren K. et al., Antibody-dependent Cellular Cytotoxicity-inducing Antibodies Against Human Immunodeficiency Virus. Presence at Different Clinical Stages, *J. Immunol.*, 1987; 139:2263–2267; Ojo-Amaize E. et al., Serum and Effector-cell Antobody-dependent Cellular Cytotoxicity (ADCC) Activity Remains High During Human Immunodeficiency Virus (HIV) Disease Progression, *J. Clin. Immunol*, 1989; 9:454–461; Lyerly H. K. et al. Human T-cell Lymphotropic Virus III$_B$ Glycoprotein (gp120) bound to CD4 Determinants on Normal Lymphocytes and Expressed by Infected Cells Serves as Target For Immune Attack, Proc. *Natl. Acad. Sci. USA*, 1987; 84:4601–4605; Katz J. D. et al. Antibody-dependent Cellular Cytotoxicity (ADCC)-mediated Destruction of Human Immunodeficiency Virus (HIV)-coated CD4$^+$ T . Lymphocytes By Acquired Immunodefiency Syndrom (AIDS) Effector Cells, *J. Clin. Immunol*, 1988; 8:453–458; Weinhold K. J. et al., Cellular Anti-gp120 Cytolytic Reactivities in HIV-1 Seropositive Individuals, *Lancet* 1988; Vol i:902–905; Weinhold K. J. et al., HIV-1 gp120-mediated Immune Suppression and Lymphocyte Destruction in the Absence of Viral Infection, *J. Immunol.*, 1989; 142:3091–3097; Tyler D. S. et al., gp120 Specific Cellular Cytotoxicity in HIV-1 Seropositive Individuals. Evidence for Circulating CD16$^+$ Effector Cells Armed in vivo With Cytophilic Antibody, *J. Immunol*, 1989; 142:1177–1182; Sawyer L. A. et al., Possible Beneficial Effects of Neutralizing Antibodies and Antibody-dependent, Cell-mediated Cytotoxicity in Human Immunodeficiency Virus Infection, *AIDS Res. Hum. Retroviruses*, 1990; 6:341–356; Tanneau F. et al., Primary Cytotoxicity Against the Envelope Glycoprotein of Human Immunodeficiency Virus-1: Evidence for Antibody-dependent Cellular Cytotoxicity in vivo, *J. Infect Dis.*, 1990; 162:837–843; and Tyler D. S. et al., Alterations in Antibody-dependent Cellular Cytotoxicity During the Course of HIV-1 Infection. Humoral and Cellular Defects, *J. Immunol.*, 1990; 1449:3375–3384). Thus, ADCC is directed against intact gp120 that is adsorbed to CD4 molecules on uninfected cells (Lyerly H. K. et al., Weinhold K. J. et al., Tyler D. S. et al. and Tyler D. S. et al., supra).

The net change in CD4 cell number is the sum of cytolytic immune responses causing lysis of infected cells and lysis of uninfected cells, added to the ability of the immune system to replace or reconstitute the lost CD4 cells. Reconstitution of lost CD4 cells may be affected by the loss of thymic hormones (Seemayer T. A. et al., Precocious Thymic Involution Manifest by Epithelial Injury in the Acquired Immune Deficiency Syndrome, *Hum. Pathol.*, 1984; 15:469–474; and HIV infection of the bone marrow precursors Folks T. M. et al., Infection and Replication of HIV-1 in Purified Progenitor Cells of Normal Human Bone Marrow, *Science*, 1988; 242:919–922) (Sun N. C. J. et al. Bone Marrow Examination in Patients With AIDS and AIDS-related Complex (ARC), *Am. J. Clin. Pathol.*, 1989; 92:589–594; and CTL activity is then, on the whole, more beneficial than ADCC, since lysis of uninfected CD4 cells is not likely to occur with CTL. ADCC has been proposed as an important factor in CD4 depletion, since both infected and uninfected cells can be lysed (Lyerly H. K. et al., Katz J. D. et al., Weinhold K. J. et al., Weinhold K. J. et al., and Tyler D. S. et al., supra).

Lysis of infected CD4 cells through direct viral lysis or programmed cell death is a direct function both of viral load and changes in viral phenotype (Tersmette M. et al., Evidence For a Role of Virulent Human Immunodeficiency Virus (HIV) Variants in the Pathogenesis of Acquired Immunodeficiency Syndrome: Studies on Sequential Isolates, *J. Virol.*, 1989; 63:2118–2125; and Connor R. I. et al., Increased Viral Burden and Cytopathicity Correlate Temporally With CD4+ T-Lymphocyte Decline and Clinical Progression in Human Immunodeficiency Virus Type 1 Infected Individuals, *J. Virol.*, 1993; 67:1772–1777). Viral pathogenic effects exhibit kinetic curves that differ from immune-mediated CD4 cell destruction, in that increases in viral load increase, rather than decrease, the rate of CD4 destruction (Wei X. et al., Viral Dynamics in lluman Immunodeficiency Virus Type 1 Infection, *Nature*, 1995; 373:117–122; Ho D. D. et al., Rapid Turnover of Plasma Virions and CD4 Lymphocytes in HIV-1 Infection, *Nature*, 1995; 373:123–126; and Coffin J. M. HIV Population Dynamics in vivo: Implication sfor Genetic Variation, Pathogenesis, and Therapy, *Science*, 1995; 267:483–489). In contrast, immune-mediated CD4 cell destruction would decline with progressive immunodeficiency, leading to the observed slowing of the rate of CD4% decline at low CD4 cell counts and percentages.

ADCC activity can be measured in vitro using two different assays. In the indirect or CMC or classic ADCC assay, peripheral blood mononuclear cells (PBMC) from uninfected individuals are used as effectors against HIV-infected or gp120-adsorbed target cells (Rook A. H. et al., Katz J. D. et al., and Sawyer L. A. et al., supra). A sample of test serum from each infected individual is added to prelabeled target cells, so that PBMC-mediated lysis is measured by release of $^{51}$Cr from target cells. This assay thus measures the humoral component of the patient's capacity for ADCC.

The cell mediated cytotoxicity (CMC) or direct ADCC assay, on the other hand, measures the ability of PBMC from infected patients to lyse a gp120-coated or HIV-infected target cell (Weinhold K. J. et al., Tyler D. S. et al., and Tyler D. S. et al., supra). CMC lysis is mediated by the patient's NK cells, armed in vivo with immune complexes; no additional antibody or other humoral component is added to either targets or effectors (Weinhold K. J. et al., Tyler D. S. et al., supre). This assay measures both the humoral and cellular components of ADCC, and thus more accurately reflects the in vivo situation (Tyler D. S. et al., supra). We will use the term "ADCC" to refer to in vivo activity, and "indirect ADCC" and "CMC" to refer to activities as measured in the two respective in vitro assays just described.

The two assays differ importantly in the ability to utilize monomeric antibody. The FcγIII receptor on NK cells is a low affinity receptor that binds IgG in immune complexes or IgG coating a virus infected cell, but does not bind monomeric IgG (Trinchieri G. et al., supra; and Unkeless J. C., Function and Heterogeneity of Human Fc Receptors for Immunoglobulin, *J. Clin. Invest.*, 1989; 83:355–61). The indirect ADCC assay, by binding antibody directly to the target, measures lysis by monomeric antibody (Trinchieri G. et al., supra). CMC, on the other hand, measures the level of the patient's NK cells that were pre-armed in vivo with immune complexes.

Differences between these two assays may explain the poor correlation of indirect ADCC activity with stage or progression of HIV disease. In general, high levels of indirect ADCC activity are found in most individuals, regardless of stage of disease or rate of disease progression (Ojo-Amaize E., et al., supra). In some studies, a small protective effect of indirect ADCC activity is suggested (Rook A. H., et al.; Ljunggren K., et al.; and Sawyer L. A., et al., supra). By using normal effectors, HIV-related defects in NK function are not considered. In addition, interpatient variability in the number of NK cells and inherent NK lytic ability may affect indirect ADCC measurements. Most importantly, since monomeric ADCC-mediating antibody can be measured in this assay, it does not reflect the availability of gp120 to both form immune complexes (and thus mediate CMC) or to sensitize an uninfected CD4 cell.

The protective role of ADCC changes with disease progression to a pathogenic role. ADCC, mediated either by monomeric antibody or immune complexes, may play an important protective role in early HIV disease by lysing infected cells and limiting the actively replicating, cellular burden of HIV. In patients with the highest CD4 percentages, infected cell burden is low; both monomeric antibody and immune complexes may mediate ADCC and contribute to a protective effect. As viral load and free gp120 increase, the target of ADCC may increasingly be gp120-coated uninfected CD4 cells, and the net effect of ADCC may become pathogenic, contributing to disease progression.

The Immunopathogenic Role of ADCC

CMC activity is mediated by immune complexes since gp120 antigen is actively being produced. If sufficient free, uncomplexed gp120 is present, it binds specifically to the CD4 molecule on uninfected CD4 cells (Lyerly H. K. et al., supra; Weinhold K. J. et al., supra; and Weinhold K. J. et al., supra). This gp120-coated CD4 cell can then be lysed either by monomeric antibody or immune complex-mediated ADCC.

Serial CMC activity in 21 asymptomatic HIV-infected patients in the Examples below showed a strong correlation between high levels of CMC activity and rapid declines in CD4 percentage. Thus effector cells are capable of lysing gp120-bearing CD4 cells in vivo; in some cases, the magnitude of CD4 loss shows that uninfected, as well as infected, CD4 cells are destroyed. Subjects with highest CD4 percentages and low CMC activity also showed very low viral burden by several assays; this suggests that insufficient gp120 was produced in those subjects to form immune complexes or to adsorb to uninfected CD4 cells.

III. A Model for the Immunoprotective and Immunopathogenic Roles for ADCC

These results are the basis of the model which is a feature is the present invention describing the immunoprotective and immunopathogenic effects of CMC to CD4 percentage decline and HIV load. In this model, four post-seroconversion stages are observed, described here and in Table 1 below:

TABLE 1

A Model for Four Post-Seroconversion Stages of HIV Disease

| Stage | 1 | 2 | 3 | 4 |
|---|---|---|---|---|
| in vitro indirect ADCC | +++ | +++ | +++ | ++/+++ |
| in vitro CMC | 0 | +++ | +++ | + |
| immune complexes | 0 | +++ | +++ | ++/+++ |
| NK effector function | 0 | +++ | +++ | + |
| in vivo ADCC | | | | |
| free gp120 | 0 | 0 | +++ | +++ |
| protective | yes | yes | yes | no |
| pathogenic | no | no | yes | no |
| in vivo target | | | | |
| infected cells | yes | yes | yes | no |
| uninfected cells | no | no | yes | no |
| CD4 decline | 0/slow | 0/slow | rapid | slow |
| HIV RNA viral load | 0 | + | ++ | +++ |
| HIV DNA proviral burden | + | ++ | +++ | +++ |

Stage 1. Antibody excess. During clinically asymptomatic HIV infection, circulating HIV DNA (cellular) burden and RNA (replicating) burden are both low, and CD4 percentage is high and stable. At low concentrations of free gp120, a state of "antibody excess" is present. Neither gp120-coated CD4 cells nor immune complexes are observed. Indirect ADCC antibody (monomeric antibody binding to targets) activity becomes high if sufficient viral antigen to stimulate production of antibody is present; in vivo these antibodies sensitize and lyse infected cells only (protective ADCC). CMC activity is low in the absence of immune complexes. Other measures, such as NK number and function, are normal.

Stage 2. Immune complexes. With progressive viral replication, low levels of gp120 are produced which are complexed with antibody to gp120 (according to stoichiometric requirements specific to that antigen and antibody). CMC activity is high as immune complexes are bound to normally functioning NK cells; indirect ADCC activity is also high. CD4 cell lysis, primarily directed against HIV-infected CD4 cells, is beneficial or protective, and contributes to stability of low viral load levels. Little excess gp120 is available to bind uninfected CD4 cells; thus, uninfected CD4 cells are not lysed by either monomeric antibody ADCC (indirect ADCC activity) or by immune complex ADCC (CMC activity), and CD4 count remains stable or declines slowly.

Stage 3. Antigen excess. Progressive viral replication leads to increased gp120, to immune complex formation and to binding of gp120 to uninfected CD4 cells. In vitro, both CMC (immune complex) and indirect ADCC (monomeric antibody) activities are high. In vivo, ADCC lyses both infected and uninfected gp120-coated CD4 cells, leading to progressive and rapid CD4 decline.

Stage 4. Effector cell dysfunction. At low CD4 percentages, cytokine disregulation leads to NK cell dysfunction and loss of CMC activity. Although in vitro indirect ADCC remains high (the antibody component), the decline in CMC activity is a more accurate reflection of ADCC in vivo. A major feature of the invention is the discovery that, as CMC decreases, the rate of CD4 decline slows, since the immunopathogenic effect of ADCC is lost. Thus HIV load increases rapidly, yet the rate of CD4 destruction slows.

IV. Components of the Model

Cell surface binding antibodies. A use of the model is the prediction that the protective antibody response is directed against the envelope glycoprotein as expressed in its native conformation on the surface of infected cells. When gp120/gp41 antibody is quantified by Western blot or ELISA, native conformation of the antigen is frequently lost. In addition, hidden epitopes and neoantigens are created which can artificially alter the results. Cell surface antibodies can be quantified by end point dilution or by a measure termed Mean Fluorescence Intensity Ratio (MFIR), which uses a human monoclonal antibody specific for the CD4 binding site of gp120 specific for the CD4 binding site (F105) to measure relative expression of gp120/41 on the cell surface (Cavacini L. et al., Loss of Serum Reactivity With the F105 Epitope in HIV-1 Infected Patients: Association With Prognosis and Viral Neutralization, *J. Acquir. Immun. Defic. Syndr.*, 1993; 6:1093–1102). This measure does not correlate with anti-gp120 and anti-V3 loop antibody measured by ELISA (Cavacini, et al., unpublished observations).

Antibodies to the CD4-binding site of gp120. The presence of antibody to the CD4 binding site of gp120, capable of blocking gp120 binding to CD4 cells, is predicted by the model of the instant invention, to prevent ADCC-mediated destruction of gp120absorbed, uninfected CD4 cells and should direct specific lysis of infected cells. The human monoclonal antibody, F105, has been shown to inhibit the binding of free virus, free gp120 and viral-associated p24 to target cells Posner et al., An IgG Human Monoclonal Antibody Which Reacts With HIV-1/gp120, Inhibits Virus Binding to Cells, and Neutralizes Infection, *J. Immunol.*, 1991; 146:4325–4332; and Montefiori et al., V3-Specific Neutralizing Antibodies in Sera From HIV-1 gp160-Immunized Volunteers Block Virus Fusion and Act Synergistically With Human Monoclonal Antibody to the Conformation-Dependent CD4 Binding Site of gp120, *J. Clin. Invest.*, 1993; 92:840–47). CD4 binding site antibodies do not bind to gp120 attached to uninfected cells, either from laboratory isolates or primary isolates (Posner et al., supra; and Zolla-Pazner S. et al., Serotyping HIV-1 Primary Isolates From Diverse Geographic Locations Using Flow Cytometry, *National Cooperative Vaccine Development Group Meeting*, Nov. 6–9, 1994). Antibody directed to the CD4 binding site epitope of gp120 expressed on infected cells is measured using the F105 blocking assay. Loss of naturally occurring CD4 binding site antibodies predicts disease progression and CD4 decline (Cavacini L. et al., supra), and increase in F105 blocking activity over time predicts continued patient stability (Cavacini L. et al., supra).

Antibodies which block binding of radiolabelled, free gp120 to CD4-positive cells were consistently present in a group of HIV-vaccinees, and CD4 binding site antibodies, measured in the F105 blocking assay, were consistently absent. Thus this assay detects functionally distinct antibodies (Posner M., supra).

Antibodies to the CD4 binding site such as F105, play a potentially important therapeutic role in modulating in vivo ADCC activity. Therapy with a human CD4 binding site antibody may 1) neutralize circulating virus, thereby reducing infection of new cells and production of gp120; 2) limit pathogenic ADCC by preventing binding of free gp120 to uninfected CD4 cells; 3) direct ADCC of infected cells; and 4) accomplish the above without directing lysis of gp120-adsorbed, uninfected cells, since the CD4 binding site epitope on gp120 is involved in gp120-CD4 binding.

Data from the Examples below show that in vitro CMC activity, in the presence of sufficiently high viral load to produce free gp120, reflects in vivo ADCC directed against uninfected CD4 cells. This is thus a factor in the CD4 decline associated with progressive HIV disease.

The invention is further illustrated by the following examples, which should not be construed as further limiting. The contents of all references, pending patent applications are published patents, cited therought this application are hereby expressly incorporated by reference.

EXAMPLES

The following methodology described in the Materials and Methods section was used throughout these Examples, set forth below.

Parameters

NK cell number

Enumeration of effector cells bearing the $CD3^-/CD16^+$, $CD56^+$ phenotype was accomplished by flow cytometric analysis. Monoclonal antibodies we obtained from Becton-Dickinson (Mountainview, Calif.).

NK cell lytic function

Peripheral blood mononuclear cells (PBMC) were isolated, washed and plated at effector: target (E:T) ratios of 50:1 and 101: with $^{51}$Cr-labelled K562 target cells in a standard NK assay. Supernatants were harvested afler 4 hours of incubation and the radioactivity in the supernatant was determined. K562 cells (ATCC CCIL-243, Rockville Pike, Md.; Lozzio et al., *Blood* 45:321–334, 1975) are a continuous line from a chronic myelogenous leukemia, and are highly sensitive in vitro target for the NK assay.

Effector Arming

The inability of effector cells from patients with low CMC activity to lyse gp120-coated target cells is a function of inability of NK cells to be armed with immune complexes and subsequently lyse gp120 coated targets. The arming assay was performed as described by Tyler D. S., et al., supra. PBMC from HIV infected patients were washed five times and incubated with heat-inactivated, undiluted test serum for one hour at 37° C., 5% $CO_2$. After an additional five washes, armed effectors were combined with gp120-adsorbed, $^{51}$Cr-labelled CEM.NK$^R$ cells, prepared as described for the CMC assay, or CEM.NK$^R$ cells chronically infected with HIV-1-$_{IIIB}$ at an E:T ratio of 100:1. For each assay, PBMC armed with a positive control pool from three patients with high CMC activity, PBMC armed with heat-inactivated autologous serum and PBMC incubated in RPMI media containing 10% fetal calf serum without added human sera ("no antibody"), were used as controls.

Effector ADCC

A low level of in vivo ADCC, and in vitro CMC, is related to an inability of effector cells from HIV-infected patients to mediate either immune complex or monomeric IgG-mediated lysis of gp120-bearing targets. The ability of effectors from patients to mediate lysis of gp120-adsorbed, CEM.NK$^R$ targets was evaluated in a standard indirect ADCC assay (Weinhold K. J., Non-restricted Forms of Anti-HIV-1 Cytotoxicity in Techniques in HIV Research, Eds. a. Aldovinin and B. D. Walker, New York: Stockton, pp. 187–199), using the identical control pool of high CMC sera used in the effector arming assay with IIIB and SF2 strains of HIV. In this assay, a 1:2,000 dilution of sera was combined with $^{51}$Cr-labelled targets, and effectors were added at E:T ratios of 50:1 and 10:1. Wells with targets and autologous sera, wells with targets and detergent, and wells with targets alone, served as controls. Release of radioactivity into the supernatant was measured following a 6 hour incubation. Specific release (SR) was calculated as:

$$\frac{CPM_{test} - CPM_{spontaneous}}{CPM_{max} - CPM_{spontaneous}} \times 100$$

env-specific ADCC activity was calculated as:

$$\%SR_{(gp120/CEM.NK^R)} - \%SR_{(CEM.NK^R)}$$

Since the "no antibody" control may be high (with NK effectors pre-armed in vivo), these results were not subtracted from ADCC results using pool antibody; rather an in vitro measure of ADCC using autologous antibodies (CMC and no antibody effector ADCC) was compared to similar measurements using pool antibody, to evaluate whether a relative lack of ADCC-mediating antibodies existed in a given individual.

Indirect ADCC activity

One component of in vivo ADCC is the presence of immune complexes and monomeric IgG that binds to a gp120-bearing target and directs NK-mediated lysis. The ability of anti-gp120 antibodies to mediate lysis of gp120-adsorbed CEM.NK$^R$ targets by normal effectors is measured using a standard ADCC assay (Weinhold K. J., supra). Targets were combined with a 1:2,000 dilution of sera, to which normal PBMC effectors were added at E:T ratios of 50:1 and 10:1. Lysis of HIV-infected targets by indirect ADCC was measured using CEM.NK$^R$ cells chronically infected with HIV-1$_{IIIB}$. Expression of HIV gp120 on the surface of infected cells was monitored using polyclonal mouse sera to gp120, followed by flow cytometry. Uninfected CEM.NK$^R$ cells, autologous serum and targets incubated with serum without effectors served as controls. Net ADCC activity was calculated as in the effector ADCC and arming assays.

CD4-binding site antibodies

The flow cytometric assay to measure F105 blocking was performed as published (Cavacini L. et al., supra). Samples of HIV-1 infected cells were incubated with sera from HIV-infected individuals (HIVS) at the appropriate dilutions for 30 minutes, 4° C., followed by washing with cold phosphate buffered saline (PBS). A minimal serum dilution of 1:50 was required to prevent non-specific effects. For all experiments, three negative control normal human sera (NHS) were used to establish a negative baseline, and purified F105 was used to establish quantitative values as a positive control. Cells were incubated for 30 minutes at 4° C. with biotin-labelled F105, and were then washed, and FITC-conjugated streptavidin (Caltag, San Francisco, Calif.) was added. After a 30 minute incubation at 4° C., cells were washed and fixed in 1% paraformaldehyde. Samples were acquired on a FACScan and analyzed using LYSYS II software to determine mean fluorescence intensity (MFI). Percent inhibition is determined by:

$$\frac{(F105\ MFI_{NHS}) - (F105\ MFI_{HIVS})}{F105\ MFI_{NHS}} \times 100$$

A blocking titer, if indicated, was performed by titering sera and performing the blocking assay.

Cell surface binding antibodies

Measurement of total serum IgG antibody reactivity with HIV-1 infected cells was performed as follows. HIV-infected cells were incubated with serum (diluted 1:50), for 30 minutes at 4° C. After washing, cells were stained with FITC-labelled goat F(ab')$_2$ anti-human IgG, Fc specific (Accurate Chemical, Westbury, N.Y.). Cells were fixed with 1% paraformaldebyde and acquired on a FACScan (Becton Dickinson, Mountainview, Calif.) with analysis using LYSYS II software. As a negative control to determine background fluorescence, HIV-infected cells were incubated with NHS, diluted 1:50, rather than with test sera. A fixed concentration of F105 (20 $\mu$/ml) and HIV IG (50 $\mu$g/ml) were included in all experiments. MFIR was calculated as the ratio of the MFI of the test sample to MFI of the F105 standard against the infected cell line.

Serum Arming

The ability of immune complexes in sera from HIV-infected patients to arm normal effectors was measured in the serum arming assay. Peripheral blood mononuclear cells (PBMC) from HIV-seronegative donors were incubated with a high CMC serum pool or autologous sera, and utilized in the arming assay, as described above ("effector arming"), using "mock armed" effectors as a control.

The requirement for the presence of immune complexes in sera to arm normal effector cells in the arming assay was evaluated by the following procedure. Sera of high arming activity was subject to ultracentrifugation to pellet immune complexes. Supernatant sera were subsequently tested for residual arming activity. The requirement for gp120 in immune complexes to mediate CMC and arming activity was evaluated by addition of increasing concentrations of gp120 to sera identified to have high indirect ADCC activity but low arming activity.

Free gp120 and gp120 in immune complexes

Several methods for determination of free gp120 in serum were used, using ELISA methods. Previously published assays have utilized polyclonal antisera (Oh S. K. et al., Identification of HIV-1 Envelope Glycoprotein in the Serum of AIDS and ARC Patients, *J. Acquir Immune Defic Syndr*, 1992; 5:251–256), monoclonal antibodies (Moore J. P. et al., Sensitive ELISA for the gp120 and gp160 Surface Glycoproteins of HIV-1, *AIDS Res. Human Retroviruses*, 1988; 4:369–379), Galanthus nivalis agglutinin (GNA) (Weiler B. E. et al., Human Immunodeficiency Virus: Novel Enzyme-linked Immunoassays for Quantitation of Envelope Glycoprotein 120, *J. Virol Meth.*, 1991; 32:287–301) and soluble CD4 (Gilbert M. et al., *J. Clin. Micro.*, 29:142–147) to capture free gp120. Monoclonal or polyclonal antibodies were then used for detection. The GNA assay is currently used for the detection of gp120 in HIV-infected cell cultures. A commercially available, sCD4-based, gp120 ELISA kit for testing of human sera samples is available (AGMED Inc., Bedford, Mass.). Although these assays detect as little as 50–100 pg of gp120 in a culture supernatant, the sensitivity of the assay is reduced in the presence of human sera from HIV-infected or uninfected adults (Gilbert M. et al., Enzyme-lined Immunoassay For Human Immunodeficiency Virus Type 1 Envelope Glycoprotein 120, *J. Clin. Microb.*, 1991; 29:142–147; and Moore J. P. et al., Sensitive ELISA For the gp120 and gp160 Surface Glycoproteins of HIV-1,

*AIDS Res. Human Retroviruses*, 1988; 4:369–379). Free gp120 has been detected in sera from patients with HIV, predominantly in late stage disease, at concentrations determined to be between 10 and 100 ng/ml (Oh S. K. et al., supra). The methods of the instant invention of CMC-mediated CD4 depletion enables selection of patients with high probabilities of having circulating gp120, i.e., those with high viral load in stages 3 and 4. If necessary, a more sensitive method to measure serum gp120 in the study population is available, and uses the AMPAK-II ELISA amplification system (Novo Biolabs Ltd, Cambridge, United Kingdom; Macy E. et al., Enhanced ELISA: How to Measure Less than 10 Picograms of a Specific Protein (Immunoglobulin) in Less than 8 Hours, *FASEB J.*, 1988; 2:3003–3009; Moore J. P., et al., supra), or a similar kit from GIBCO (Grand Island, N.Y.). Initial determinations of gp120-specific immune complexes used a modification of the gp120 ELISA described above. Once sensitivity of the gp120 ELISA is optimized, the assay can be modified by using a monoclonal antibody to the Fc portion of IgG, to detect immune complexes containing gp120 (Oh S. K. et al., supra).

Data is analyed by comparing activity of cells and antibody in mediating the various components of CMC in patients analyzed into one of the 4 stages of the model. Data indicate differences between high and low CMC patients and those with rapid or slow CD4% decline and allow tests of the models in a statistically rigorous manner. Changes in these measurements in response to antiretroviral therapy is also recorded.

Statistical analysis

The significance of the various components of CMC to net CMC activity is evaluated using multivariate methods. These consist of a multiple regression model with net CMC as the dependent variable and the components of CMC constituting the independent variables. A stepwise model building procedure is used to determine an appropriate model. Standard transformation methods are used to improve model fit. The estimated model is evaluated using standard regression diagnostics such as examination of residuals. In addition, free or immune-complexed gp120 measurements rather than viral load is used to determine CMC activity in the model CMC=CD4%+gp120 and for predicting CD4% decline in model CD4% decline=CMC×gp120. These models are re-analyzed with data from gp120 measurements.

Analysis of the characteristics of patients with differences in CMC activity identifies characteristics associated with rapid or slow CD4% decline. Such characteristics, e.g. low percentage of $CD3^-/CD16^+,56^+$ cells, predispose to low CMC activity and relative preservation of CD4 count. Intrinsic markers, such as NK cell percentage, are used as prognostic markers. Other markers, influenced by stage of disease, such as NK lysis of K562 cells or circulating viral load suggest appropriate timing of specific therapies to reduce the pathogenic effect of ADCC on CD4 cell number and percentage.

A group of long term non-progressors is evaluated by the above laboratory measures (CMC, RNA PCR, DNA PCR and components of CMC), to determine whether non-progression is characterized by defects in the effector cell or antibody components of CMC. Longitudinal follow-up of individuals is used to compare the characteristics of individuals who remain stable, in comparison to individuals of similar initial characteristics who progress, in order to determine whether non-progressors comprise a continuum of responses or comprise a separate subgroup. For patients described in Examples with the longest follow-up (nearly 4 years), it cannot yet be determined whether these individuals will not progress, or simply have not yet progressed. Patient samples include individuals with rapid and slow CD4% decline. These patients have been partially matched, since both rapid and slow CD4% decliners had greater than 400 $CD4$ cells/$mm^3$ at the time of entry into the study.

Comparison group consists of individuals with extreme long-term non-progression, i.e., individuals with infection documented for at least 7 years, who have maintained CD4 cell counts over 500 in the absence of antiretroviral therapy or clinical HIV disease or symptoms.

Long term non-progressors are identified by practitioners from two clinical practices, and by using databases from longitudinal cohort studies. Individuals are asked to participate in the study based on a consideration of both lack of CD4 decline (in the absence of antiretroviral therapy or symptoms) and duration of follow-up, with a goal toward equal gender distribution. PBMC and sera are available frozen from individuals enrolled as early as 1985 in Fenway studies, and fresh samples are assayed as they are acquired. All individuals followed at the study sites have clinical and CD4 cell data obtained at 6 month sampling intervals. Patients identified as extreme long-term non-progressors are evaluated for the study by the study nurse coordinator.

Clinical data from each patient include: age, gender, history of previous HIV-related illnesses or symptoms (if any), previous exposure to antiretroviral agents, and CD4 cell count and percentages. Women who are pregnant are enrolled 6 months or more following delivery.

Descriptive analysis of primary infection

In many individuals with primary infection, rapid falls in CD4 cell count occur, coincident with high viral loads; CD4 counts rebound and viral load rapidly falls, often to undetectable levels, in the absence of antiretroviral treatment. ADCC lysis of infected cells contributes to this CD4 decline and control of each of viral replication (perhaps by CTL responses), CMC, and arming activity. Arming activity, ADCC activity and free and immune-complexed gp120 are assayed during early seroconversion, to describe the time course of changes in these measures and as they relate to a changing slope of CD4% decline.

Long-term non-progressors

Serially collected, frozen sera from epidemiologic cohorts can span 7 to 10 years for a given individual. Serial assays of arming and ADCC activity, and free and immune complexed gp120 describe these measurements in long-term non-progressors over long-term follow-up.

Rapid CD4 decliners

Changes in arming and ADCC activity, free and immune complexed gp120 are described over the period of rapidly declining CD4% in these patients.

Monoclonal Antibody (F105) Therapy

Changes in arming, ADCC and free and immune-complexed gp120 are assayed from samples collected before and after single-dose infusion of F105. Data are expressed with respect to changes in CD4% and measured serum concentrations of F105 at each timepoint.

Active clinical cohorts

The Miriam Immunology Center. Seventy-seven percent of the patients with HIV seen at this site are women. Sixty-one percent of the women are Caucasian, 18% African American and 20% Latina. Approximately half of the women contracted HIV through heterosexual contact, the other half through intravenous drug use. Over sixty percent of the women are asymptomatic. Stratogen Health Center. This primary care practice follows approximately 300 predominantly gay (80%), white (90%) and male (95%) patients. Between the Stratogen and the Miriam Immunology Center, a representative and balanced sample of individuals infected with HIV in Rhode Island is available. Minorities are not excluded, either from the practice or the study.

Retrospective cohorts

Fenway Community Health Center Cohort: This is a cohort of gay predominantly white men (93%), formed when such a population had the greatest incidence of HIV infection. Samples dating to 1985 are not available from other cohorts in the area. New England Behavioral Health Study: This is a cohort of individuals who, on enrollment, identified themselves to be at increased risk for heterosexual transmission of HIV. Eleven percent of the cohort is African American and 10% are Latino. One third of the cohort members identified themselves as former or current intravenous drug users. Twelve hundred men and 800 women were enrolled. This cohort of individuals heterosexually infected or at risk to become so, is one of the earliest identified heterosexual cohorts. The patient population enrolled in the study, in fact, over-represent minorities in the community, a reflection of the demographics of HIV disease in Rhode Island. Individuals participating in this study donate blood samples two to three times per year. A maximum of 70 ml of blood is drawn; complete blood counts and T lymphocyte enumeration are performed as part of this study. Uninfected donors are recruited from laboratory and hospital employees, and blood is drawn up to 4 times per year. HIV-infected individual recruits discuss the study with the study nurse coordinator and give informed consent. Patients identified from cohort databases are asked to participate, and consent is obtained. All data bearing patient identifiers are handled according to hospital confidentiality policies. In addition, files in the clinical trials office are kept in a secure room which is locked when unoccupied.

MATERIAL AND METHODS

Assays

Cell mediated cytotoxicity (CMC Assay)

The CMC assay was performed as published by (Weinhold K. J. et al., supra; and Weinhold K. J., Non-restricted Forms of Anti-HIV-1 Cytotoxicity in Techniques in HIV Research, Eds. A. Aldovini and B. D. Walker, New York: Stockton, pp. 187–199), and modified as described (Skowron G. et al., High Levels of Cell-mediated Cytotoxicity (CMC) Correlate With Rapid $CD4^+$ Cell Decline. 34th International Conference on Antimicrobial Agents and Chemotherapy, Orlando, Fla. Oct. 4–7, 1994). PBMC were isolated by Ficoll density gradient centrifugation from samples collected into anticoagulated tubes, preferably acid-citrate-dextrose (ACD) tubes, however heparin-or EDTA-treated tubes are also used. Isolated PBMCs were washed and plated with $CEM.NK^R$ cells that were adsorbed with 5 microliter/ml of $gp120_{IIIB}$ (American Biotechnologies, Inc., Cambridge, Mass.), and labelled with $^{51}Cr$. Effector (E) and target (Tr) cells were combined in 96 well plates at E:T ratios of 50:1 and 10:1, and target lysis was measured after 6 hours of incubation by counting release of radioactivity into supernatants harvested using a Skatron harvester. Percent lysis was calculated as:

$$\frac{CPM_{test} - CPM_{spontaneous}}{CPM_{max} - CPM_{spontaneous}} \times 100$$

Percent gp120-specific lysis (CMC activity) was calculated as:

$$\%lysis_{gp120/CEM.NK}{}^R - \%lysis_{CEM.NK}{}^R$$

CD4% determination by Flow Cytometry

Cell-surface markers were determined by the whole blood lysis technique as standardized by the College of American Pathologists. CD3, CD4 and CD8 monoclonal antibodies were obtained from Immunotech, Westbrook, Me., and cells were acquired on a Becton-Dickinson FACScan. Data were analyzed using Simulset software.

RNA PCR

Blood collected in ACD tubes was centrifuged to isolate plasma, which was then centrifuged at 1200×g for 10 minutes. Platelet-free plasma was then aliquotted and frozen at −70° C. until assay.

Quantitation of plasma HIV-1 gag RNA was performed using the RT-PCR assay (HIV-1 Monitor Test; Roche Molecular Systems, Somerville, N.J.). This assay uses a single enzyme rTth DNA Polymerase for both reverse transcription and PCR. In addition, dUTP and uracil-N-glycosylase were used to prevent carryover. An internal standard was added to each sample to monitor the efficiencies of extraction, reverse transcription and amplification.

Each amplified sample was diluted five-fold prior to detection. The PCR products were captured and quantified on 96 well microwell plates that were coated with either the internal control probe or the HIV-1 probe. The HIV copy number was determined by extrapolating the "adjusted" HIV signal from the internal control signal. This colorimetric microwell assay format was similar to the microwell plates currently used for the HIV-1 qualitative assay but was modified to provide a three log dynamic range for detection.

Quantitative DNA PCR

PBMC were isolated from ACD-anticoagulated blood by Ficoll density gradient separation and were washed and counted as described above for the CMC assay. Aliquots of $1×10^6$ cells were centrifuged, supernatant was removed and the dry pellet was frozen at −70° C. until assay. HIV-1 DNA PCR testing was performed in duplicate using cell lysates of pellets from $1×10^6$ cells, and five 5-fold dilutions of the lysate. Amplification of HIV-1 gag sequences was performed in duplicate using biotinylated SK462/431 primers to generate biotin-labeled amplicon DNA that was subsequently detected calorimetrically. The biotinylated amplicons were transferred to the wells of a 96-well microtiter plate coated with probe sequences (SK102) complementary to HIV target sequences. Detection of the hybridized amplicon was accomplished by adding streptavidin-conjugated horseradish peroxidase (HRPO conjugate). After washing to remove unbound conjugate, tetra-methylbenzidine substrate was added and reacted with the HRPO to generate color measurable at 450 nm with a spectrophotometer. HIV-1 DNA copy number standards (0, 5, 10, and 20 copies per amplification), negative and positive detection controls, extraction buffer and specimen wash controls were all included in each performance of the PCR protocol.

Serum collection and storage

Serum for ADCC and arming assays was collected, aliquotted and stored at −70° C. until use.

EXAMPLE 1

CMC Activity and Rate of CD4% Decline

Serial CMC assays were performed with samples from over 30 patients obtained since 1991 (10 women, 23 men), especially patients with initial CD4 counts over 400.

CMC activity was found to be stable at high (greater than 20) or low (less than 10) levels for at least 1 to 2 years in most patients. Repeated assays have identified patients with consistently high or low activity during a follow-up period of 3 years or more. FIG. 1A illustrates serial CMC assays and CD4% in a patient with low CMC (stage 1). Throughout 24 months of follow-up, her CMC activity ranged from 0 to 9% cytotoxicity (mean=5), and her CD4% slope over this time period was +0.4% per year. FIG. 1B illustrates the pattern of CMC cytotoxicity in a patient with high CMC (stage 3). Over a follow-up period of 16 months, his CMC activity ranged from 18 to 39% (mean=27%) and his CD4% slope was −15.1% per year.

The marked difference in rates of CD4% decline in these and other patients with high or low CMC activity suggested that a correlation existed between CMC activity and the rate of CD4 cell destruction. In an analysis of 21 patients, high mean levels of CMC activity correlated with rapid declines in CD4%, whereas low mean CMC correlated with relative stability or rises in CD4% over time (r=−0.48, p=0.03, FIG. 2A, Skowron G. et al., supra). Thus, CMC activity as measured in vitro reflected the ability of NK cells armed with antibody to gp120 to lyse gp120-coated, uninfected $CD4^+$ cells in vivo.

EXAMPLE 2

Effect of Circulating Viral Load on CD4 Lysis (stages 2, 3, and 4)

Several patients in the initial CMC versus CD4% decline analyses showed high CMC and level CD4 slope. The RNA PCR level in these patients indicated that a threshold of viral load was necessary to cause CD4 depletion. This is in agreement with the mechanism for CMC killing of uninfected CD4 cells which requires that sufficient gp120 be produced to exceed the capacity for antibodies to form immune complexes, a state of "antigen excess". Thus in a group of individuals with similar initial CD4 percentage and CMC activity, the rate of CD4 decline would depend on viral load or viral burden (as surrogate markers for gp120 production).

Figure 2A:
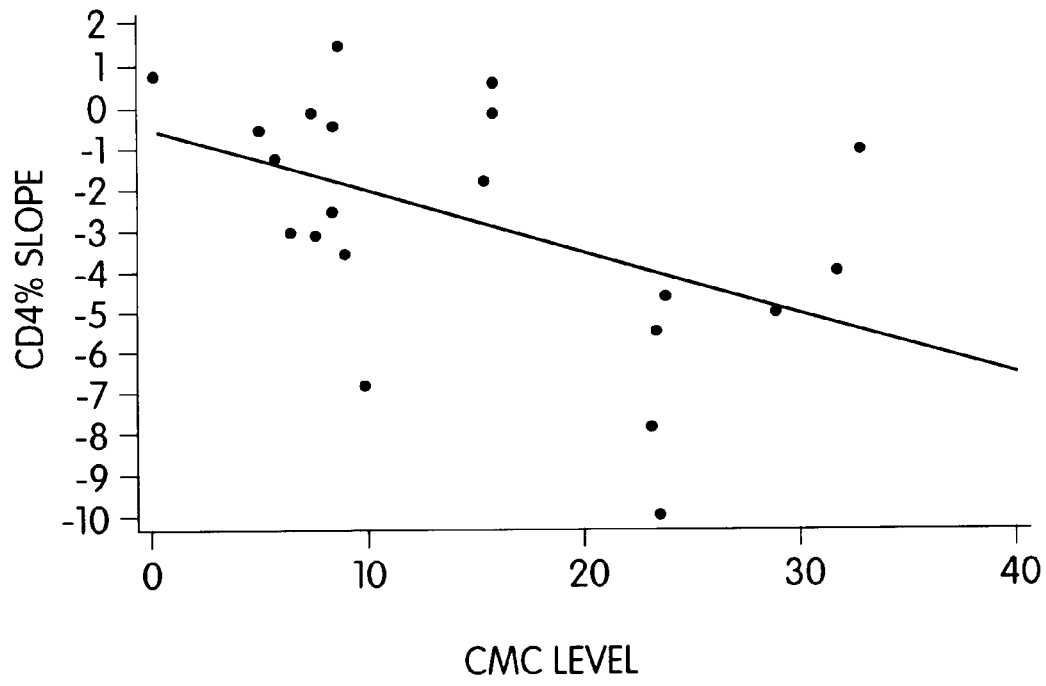
FIG. 2A shows a graphical correlation between CMC percent target lysis activity and percent CD4 change per year.
Figure 2B:
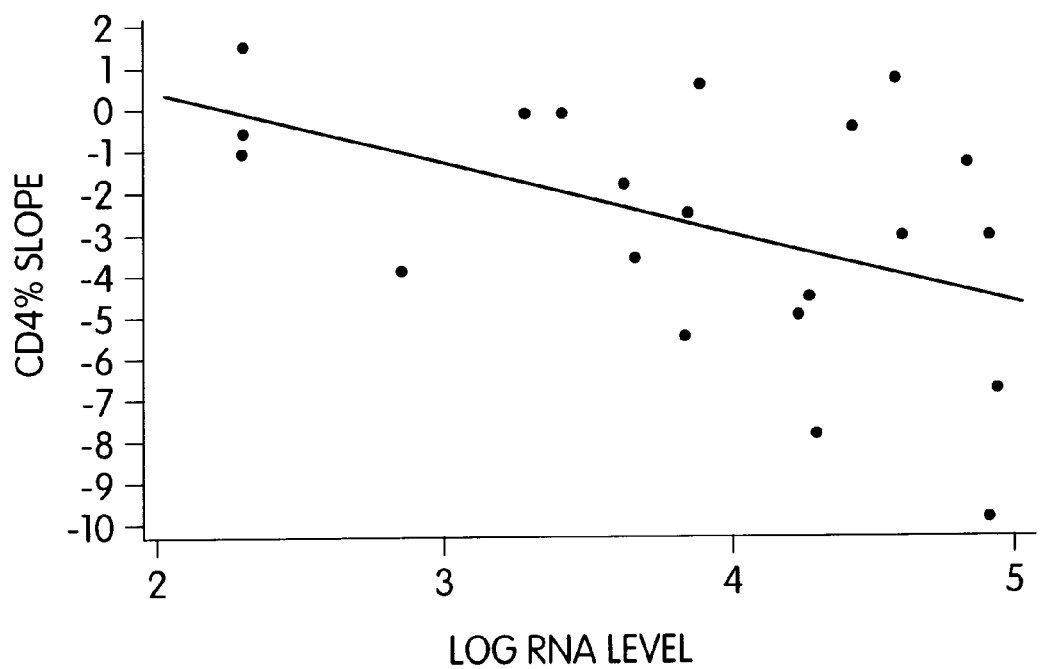
FIG. 2B shows a graphical correlation between percent CD4 change per year and log viral load, measured by RNA PCR, in 21 HIV patients.
Figure 3:
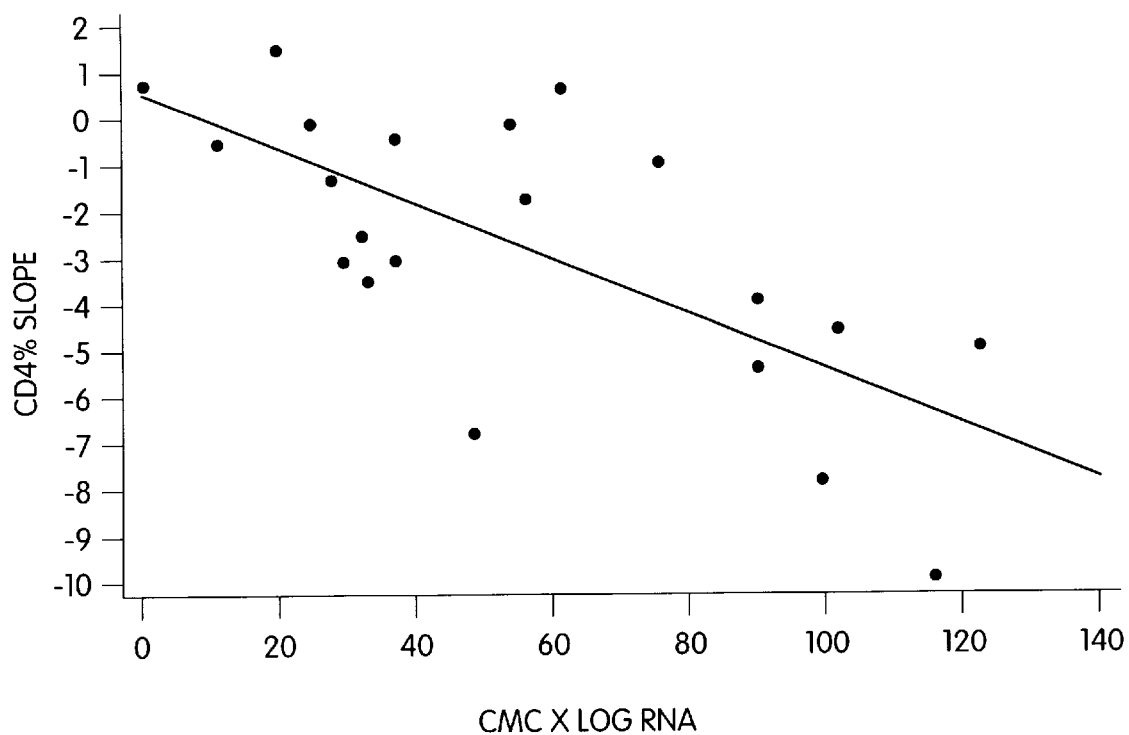
FIG. 3 is a graphical correlation of percent CD4 change in slope as a function of the product of CMC percent target lysis and log of HIV viral load, measured by RNA PCR, in 21 HIV patients.

An analysis of 21 patients, representing each of the 4 stages invented here, showed that both CMC and viral load (as measured by RNA PCR) were independently correlated with CD4% decline (for CMC, r=−0.48, p=0.03; for RNA PCR, r=−0.048, p=0.03, FIG. 2A and 2B). Some patients with either high CMC or high viral load did not experience CD4 decline, however, the algorhithm for interaction of CMC and viral load (i.e., CMC×logRNA PCR), improved the correlation substantially (r=−0;71, p=0.0003, FIG. 3).

This shows that while each of CMC and viral load are important components of the mechanism of CD4 decline, there is significant interaction of the two measurements. Furthermore, neither CMC activity nor viral load alone appears sufficient to determine rate of CD4% decline. This is illustrated in 8 patients in stages 2, 3 and 4 in FIG. 4. In stage 2 patients, high CMC, accompanied by low viral load, did not result in CD4 decline. Stage 3 patients showed high CMC and higher viral loads associated with rates of CD4 decline from −4 to −11 percentage points per year. Stage 4 patients, in contrast, exhibited low CMC and high viral load, yet CD4 percentages were stable.

Differences between viral load in stages 2 and 3 were relatively small. The requirement for a threshold of viral load for disease progression has been recently suggested by longitudinal data from the Multicenter AIDS cohort study, in which disease progression was related to viral loads greater than 10,000 copies per ml (Mellors J. W. et al., Quantitation of HIIV-1 RNA in Plasma Predicts Outcome After Seroconversion, Ann. Int. Med., 1995; 122:573–579). In addition to ADCC lysis of gp120-coated uninfected cells, the decline in CD4% in patients actively producing virus is consistent with a combination of immunologic and virologic mechanisms, including apoptosis, ADCC and CTL lysis of infected cells.

EXAMPLE 3

Circulating Viral Load is Necessary but not Sufficient to Mediate Destruction of CD4 Cells (stage 4)

Figure 4:
FIG. 4 is a bar graph showing data on the parameters CMC percent target lysis, viral load, and percent of CD4 decline in eight HIV patients, arranged by stage in disease progression.

The instant invention shows that CD4 decline in patients in stages 2 and 3 was proportional to increasing or high viral loads, in agreement with data from with other investigators showing a virologic basis for CD4 destruction. However, the relative stability of CD4 percentage in patients with severe immunodeficiency suggests that a purely virologic mechanism is unlikely. In longitudinally followed patients with CD4 percentage of 20 to 25%, low CMC activity was associated with slow or no decline in CD4 count, in the presence of high HIV loads (FIG. 4, stage 4). Many patients with low CD4 cell counts/percentages and high viral loads did not rapidly progress or experience sharp declines in CD4 percentage.

EXAMPLE 4

Determinants of High CMC Activity: CD4% and Viral Load

CMC activity in vitro requires functioning effector cells, ADCC-mediating antibodies, and sufficient gp120 to form immune complexes that can arm NK cells. Thus at very low viral loads, monomeric antibody predominated and immune complexes did not arm NK cells in vivo or in vitro. Similarly, at low CD4%, NK effector cell activity would not be sufficient to produce CMC lysis. This hypothesis can be tested with data from our current cohort, using the model:

$$CMC = CD4 + RNA\ PCR$$

For the 21 individuals analyzed above, this model demonstrated that both CD4% and RNA PCR were significant predictors of CMC activity (p=0.03 and p=0.02, respectively).

Percentage of NK cells and NK lysis of K562 cells may also determine CMC activity. The influence of the number of circulating NK cells was assessed by flow cytometry, using as the percent of circulating lymphocytes, those bearing markers associated with NK cells ($CD3^-/CD16^+$, $CD56^+$). Phenotypic analysis was matched with CMC assays performed at the same time. In a linear regression analysis, mean CMC was strongly assocated with the mean number of circulating NK cells (r=0.42, p=0.07). This shows that number of circulating NK cells is an effector component of CMC activity. Percentage of $CD3^-/CD\ 16^+$, $CD56^+$ cells remained stable in a given patient over time, and may identify individuals predisposed to mediate high level CMC activity in the presence of sufficient gp120 and antibody to gp120, defining a rapid CD4-decliner subgroup (Table 2; see additional patients in Table 3).

TABLE 2

Effect of NK cell function and number of CMC activity

| patient | stage | CD4% | envCMC | K562 lysis | 3−/16+, 56+ |
|---|---|---|---|---|---|
| JLG | 2 | 30 | 43 | 71 | 21 |
| PJP | 3 | 27 | 49 | 74 | 27 |
| WJB | 4 | 16 | 3 | 23 | 3 |
| JXG | 4 | 20 | 0 | 29 | 4 |

The influence of intrinsic NK cell lysis of a target cell was assessed in a standard NK assay against $^{51}$Cr-labelled K562 target cells. Measurements of NK lysis at an effector target ratio of 50:1 were correlated with CMC assays done at the same time. In a linear regression analysis, a correlation was observed between the mean level of CMC activity and spontaneous NK lysis of K562 cells (r=0.44, p=0.04). This suggests that the intrinsic lytic ability of NK cells was important in the effector component of CMC activity. This correlation was also seen by Tyler et al. in a larger population. The importance of NK lytic ability in determining CMC activity is illustrated by the loss of CMC at low CD4 percentage (stage 4), as the cytokine milieu is disordered (Table 2; see additional patients in Table 3).

EXAMPLE 5

Longitudinal Changes in CMC Activity (stage 1 versus stage 2) and Rate of CD4% Decline (stage 2 versus 3)

Figure 5:
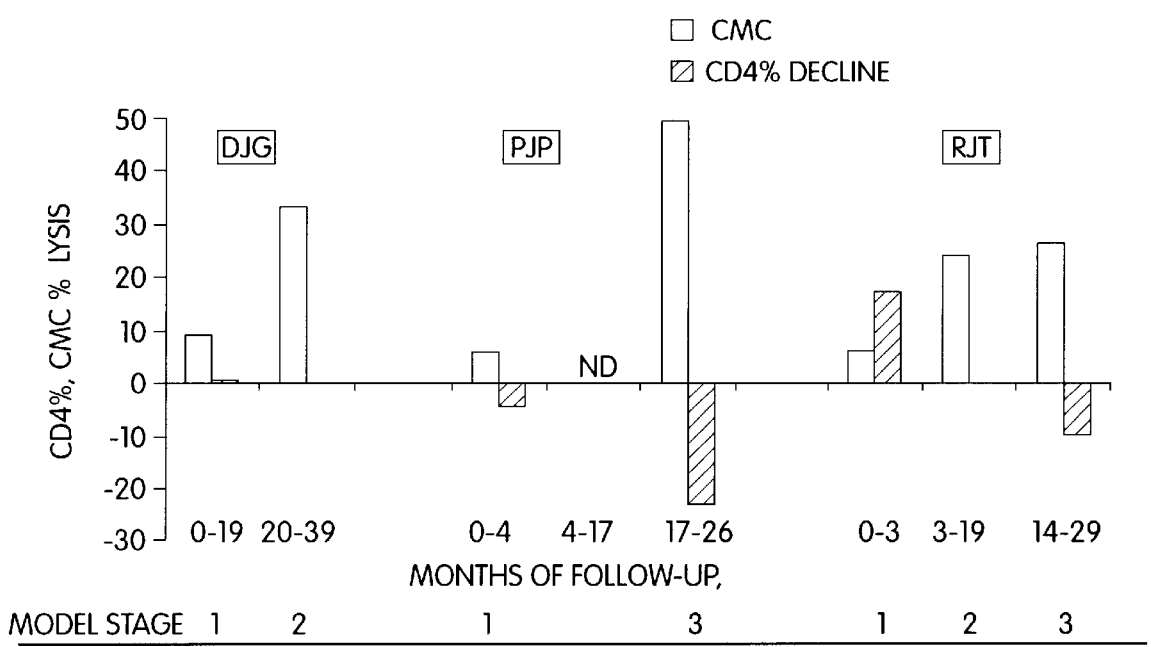
FIG. 5 is a bar graph correlating data on HIV disease progression parameters with months of follow-up and stage of disease for each of three patients.

In a small number of individuals, CMC activity changed markedly during long term follow-up studies. Three individuals had sharp rises in CMC activity over time. In two patients this coincided with rapid declines in CD4%. This shows that the 4 stages reflect progression of HIV disease, rather than distinguishing individuals who will or will not progress (FIG. 5).

EXAMPLE 6

Longitudinal Study of HIV Disease Progression

Fifteen patients followed with longitudinally using CMC data are presented in Table 3, and illustrate the four stages of HIV disease progression of this invention. It is important to note that the patients listed in Table 3 had CD4 counts over 400, for at least 2 of the first 3 samples even though CD4 percentages suggested more advanced disease stage. In addition, these data showed that within three to four years, a significant number of patients with this initial CD4 count show rapid declines in CD4 percentage. These declines in CD4 percentage took place over a period of 1 to 2 years, for a yearly loss of 4 to 5 percentage points or more per year.

EXAMPLE 7

Figure 6:
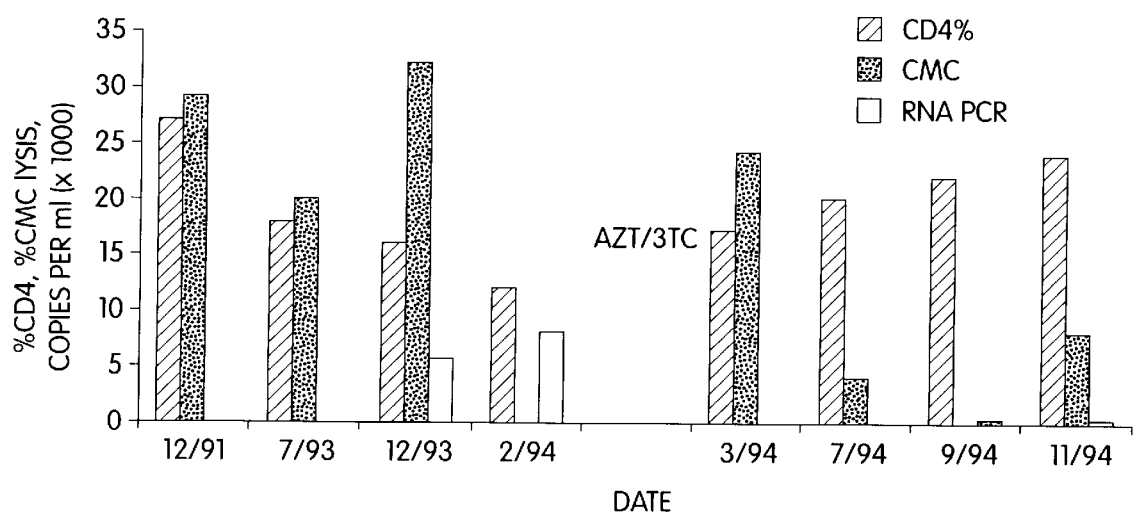
FIG. 6 is a bar graph showing the effects in an HIV patient of antiretroviral chemotherapy with AZT and 3TC, correlated with decline during therapy in CMC percent target lysis and viral load RNA PCR, and with increase in CD4%, as a function of time since inception of treatment.

Antiretroviral Therapy Reduces Viral Load and CMC Activity and Increases CD4 Percentage Several individuals initiated antiretroviral therapy during the period of observation. Serial assays of one patient (RJT) demonstrates the dependence of CMC activity on circulating viral load and the fall in CMC activity during rising CD4 count (FIG. 6). CMC activity was high ($\geq$20% lysis) from 1991 to 1993. CD4% fell during this time from 27% to 12%, with modest viral load of 5,700–8,100 RNA copies per ml. In 1994 this individual started AZT and 3TC combination therapy. His viral load quickly dropped to zero and his CD4% rose. During the first 8 months of therapy, CD4% continued to rise; of note is that CMC activity fell dramatically, correlating with an improving immune system, as evidenced by CD4 percentages. The observed fall in CMC activity demonstrated the features of present invention as viral load falls below a threshold level, the levels of both immune complex-armed NK cell effectors and gp120-coated CD4 cells is shown to fall. This loss of the immunopathogenic effect of ADCC is thus a factor contributing to CD4 cell increase as a result of effective antiretroviral therapy.

Other individuals initiating antiretroviral treatment did not demonstrate a rise in CD4%. One possible explanation for this is that viral load (and free gp120) remained above the threshold for CMC-mediated lysis of uninfected CD4 cells. Response to therapy is also dependent on the rate of CD4 production, which may vary markedly between patients at a given stage of HIV disease (Wei X. et al.; Ho D. D. et al.; and Coffin J. M. et al., supra).

TABLE 3

Four stages of HIV disease progression: data from 15 longitudinally followed patients

| Patient | initial CD4 % | initial abs CD4[1] | months of f/U[2] | mean CMC[3] | CD4 % slope[4] | NK activity[5] | CD3−/ 16+,56+[6] | RNA PCR[7] | DNA PCR[8] |
|---|---|---|---|---|---|---|---|---|---|
| stage 1. High CD4 %, low viral load, low CMC, slow/no CD4 decline |||||||||||
| DEK | 60 | 1360 | 46 | 9 | +1.1 | 55 | 7 | <0.2 | 3 |
| NM | 42 | 1010 | 27 | 5 | +0.4 | 45 | ND | <0.2 | ND |
| GPG | 30 | 580 | 22 | 8 | +0.3 | 45 | 7 | 2.3 | 76 |
| stage 2. Low and stable viral load, high CMC, slow/no CD4 decline |||||||||||
| JLG | 35 | 620 | 44 | 34 | −1.0 | 65 | 16 | <0.2 | 268 |
| DJG | 25 | 870 | 40 | 18 | +0.3 | 65 | 4 | 2.5 | 431 |
| DEB | 27 | 630 | 25 | 14 | −2.3 | 47 | 5 | 5.3 | ND |
| DBN | 40 | 440 | 24 | 32 | −3.2 | 36 | 8 | 0.8 | 78 |
| stage 3. Rising viral load, high CMC, rapid CD4 decline |||||||||||
| RAC | 28 | 670 | 31 | 23 | −4.8 | 43 | 10 | 21.0 | 1287 |
| RJT | 22 | 530 | 29 | 22 | −5.4 | 68 | 8 | 6.9 | ND |
| TPW | 42 | 550 | 42 | 28 | −5.9 | 56 | 6 | 17.4 | 1607 |
| PJP | 53 | 550 | 30 | 27 | −6.5 | 74 | 27 | 16.8 | 113 |

TABLE 3-continued

Four stages of HIV disease progression: data from 15 longitudinally followed patients

| Patient | initial CD4 % | initial abs CD4[1] | months of f/U[2] | mean CMC[3] | CD4 % slope[4] | NK activity[5] | CD3-/ 16+,56+[6] | RNA PCR[7] | DNA PCR[8] |
|---------|---------------|-------------------|------------------|-------------|----------------|----------------|------------------|------------|------------|
| MAP | 25 | 590 | 19 | 30 | −13.5 | 42 | 8 | 104.3 | 6392 |
| | stage 4. Low CD4 %, very high viral load, low CMC, slow CD4 decline | | | | | | | | |
| WJB | 23 | 400 | 27 | 6 | −1.3 | 23 | 3 | 87.4 | ND |
| DY | 14 | 324 | 28 | 8 | −0.3 | 39 | ND | 53.7 | ND |
| JXG | 16 | 1220 | 20 | 0 | +1.4 | 31 | 5 | 38.3 | 81 |

[1]Absolute CD4 cell count is expressed in cells/mm$^3$.
[2]Duration of follow-up of at least 18 months.
[3]Mean of at least 4 CMC assays, expressed as % env specific cytotoxicity (see Laboratory Methods)
[4]CD4 % slope is expressed as percentage points gained or lost per year, using a linear regression analysis.
[5]NK cytotoxicity is expressed as % lysis of $^{51}$Cr-labelled K562 target cells.
[6]CD3$^-$/16,56$^+$ cells expressed as percentage oftotal lymphocytes.
[7]RNA PCR expressed in thousands of copies per ml. The lower detection limit of the test is approximately 200 (0.2 × 10$^3$) copies per ml. An undetectable level of RNA is expressed as <0.2.
[8]DNA PCR expressed in infectious units per 10$^6$ cells.

EXAMPLE 8

Affect of Therapy with Antibody to the CD4 Binding Site of gp120 (F105)

One individual (DEB) participating in a single-dose study of the effects of gp120 CD4-binding site antibody, F105, showed a sharp drop in CMC activity, as assayed 6 weeks following the infusion. This individual had strong CMC activity prior to, and following, the detection of circulating level of F105 (Table 4). At the time of CMC assay, serum level of F105 was 7.4 µg/ml. [Gail: exactly when were the "pre" and "post" samples taken?]

TABLE 4

CMC activity before, during and after F105 therapy

| | | CMC | CD4% | RNA PCR |
|---|---|-----|------|---------|
| DEB | pre 1/6/94 | 32 | 25% | 3,877 |
| 6 wks. | F105 6/24/94 | 6 | 25% | 7,306 |
| | post 9/20/94 | 20 | 23% | 4,745 |
| MAP | pre 3/31/94 | 21 | 10% | 68,627 |
| | F105 6/16/94 | 23 | 6% | 64,000 |
| | post 9/27/94 | 18 | 4% | 206,400 |

These data, obtained from a single patient, suggested that administration of antibody to the gp120 CD4 binding site reduced ability of free, circulating gp120 to form immune complexes which subsequently bound to gp120 adsorbed to the CD4 site of uninfected CD4 cells in an in vitro CMC assay. It also shows that antibody therapy may modulate the course of HIV disease independent of the ability of F105 to neutralize primary isolates.

The lack of modulation of CMC or CD4% decline in a second patient (MAP), despite similar levels of F105 (6.5 µg/ml), was due to very high viral load, and thus high levels of circulating gp120, maintaining the condition of antigen excess despite increased levels of a beneficial antibody.

EXAMPLE 9

Relationship between CMC and Serum Arming Activity

The in vitro CMC assay measures both humoral and cellular components of in vivo ADCC activity. The arming assay measures the ability of sera to bind to and "arm" NK cells from HIV-seronegative donors, during a one hour incubation in vitro (Tyler D. S. et al., supra). Thus, in contrast to the indirect ADCC assay, the arming assay measures ability of immune complexes, and not IgG monomers, to mediate ADCC. In addition, this assay is an accurate reflection of CMC activity in early HIV disease, when effector cell dysfunction plays a minor role in determining CMC activity. The advantage of the arming assay is the ability to conveniently evaluate frozen sera collected from large, prospective cohort studies, which may contain up to 10 years of collected frozen serial samples.

EXAMPLE 10

Distinguishing Stages of Disease Progression by the Arming Assay

Initial studies suggested correlation between CMC activity of seropositive serum donors in stages 1 to 3, and the subsequent activity of seronegative PBMC armed with that same serum. Careful analysis revealed marked differences in the intrinsic lytic ability of seronegative donor NK cells (against K562 cells) and in NK number. These factors are shown here to influence CMC activity (Tyler D. S. et al., supra). We have therefore developed two methods of standardizing arming data, controlling for seronegative donor variability: a ratio of arming activity using the patient's serum, to arming of the same donor's effectors using a pool of known arming activity; and a ratio of arming activity to donor NK activity as measured by lysis of K562 cells (Table 5).

Using either a ratio of patient/pool arming or arming/NK activity, the results suggest that the arming assay is useful for distinguishing individuals with low CMC activity in stage 1, from those with high CMC activity in stages 2 and 3. Lower arming activity in stage 4 is due to presence of smaller immune complexes, in a milieu of antigen excess, arming normal NK effectors less well than those present in stages 2 and 3.

EXAMPLE 11

Serum ADCC against gp120$_{IIIB}$-coated and HIV$_{IIIB}$-infected Targets

Serum ADCC against gp120-coated targets (using normal donor effectors and serum from study patients), varied widely across the CD4% spectrum. In general, serum from all tested individuals mediated high levels of lysis of HIV-infected cells. Results were standardized against a pool of sera with demonstrated high activity in the ADCC assay, in order to decrease inter-assay variability, due to differences in normal donor effector cell activity. Using these patient sera/pool sera ratios, it was shown that in some individuals (RJT, JXG) there was a deficiency in gp120 ADCC-mediating antibody (Table 6). This is consistent with reports of lower ADCC activity in patients with later stage or progressive HIV disease (Rook A. H. et al.; Ljunggren K. et al.; and Sawyer L. A. et al., supra).

The loss of gp120-specific, but not HIV-specific, ADCC-mediating antibody represents the preservation of antibodies specific for regions of gp41, or for epitopes on gp120 expressed on the surface of infected cells, but not on cells adsorbed with gp120, such as those with the CD4 binding site of gp120 (which is not available when gp120 is bound to a $CD4^+$ target cell).

TABLE 6-continued

Serum ADCC against gp120-coated and HIV-infected targets (normal effectors)[1]

| | patient | CMC | gp120 ADCC | HIV ADCC | gp120 pt/pool | HIV pt/pool |
|---|---|---|---|---|---|---|
| stage 4 | JXG | 0 | 5 | 60 | 0.16 | 0.85 |
| | SRP | 6 | 26 | 62 | 0.52 | 0.87 |
| | WJB | 4 | 33 | — | 0.52 | — |

[1]E:T ratio for ADCC assays is 50:1

Effector cells from stage 4 patients had reduced functional activity by all measures tested. In addition, pool antibodies did not enhance either indirect ADCC or arming lysis. Taken together with the results of serum ADCC (Table 6), this shows that the defect responsible for low CMC activity in stage 4 is primarily cellular, not humoral. Individuals such as JXG, who had low levels of both effector cell activity and

TABLE 5

Ability of HIV[+] serum to arm NK effector cells from HIV-uninfected donors

| Stage | Patient | Patient CMC | Effector donor | Patient arming[1] | Pool arming[1] | donor NK activity[2] | Arming pool ratio | Arming NK ratio |
|---|---|---|---|---|---|---|---|---|
| stage 1 | NM | 8 | HMA | 1 | 13 | 24 | 0.08 | 0.04 |
| | DEK | −1 | VES | 2 | 23 | — | 0.09 | — |
| | | | FAG | 13 | 37 | — | 0.35 | — |
| | | | HMA | 5 | 22 | 72 | 0.23 | 0.07 |
| | | 9 | VES | 2 | 23 | — | 0.09 | — |
| | | 2 | GEA | 5 | — | 38 | — | 0.13 |
| | GPG | 10 | FAG | 2 | 32 | 42 | 0.06 | 0.05 |
| stage 2 | DBN | 55 | PXR | 25 | 31 | 42 | 0.81 | 0.60 |
| | | 53 | HMA | 16 | 13 | 24 | 1.23 | 0.67 |
| | JLG | 30 | PXR | 27 | 31 | 42 | 0.87 | 0.64 |
| | | 43 | GEA | 20 | — | 38 | — | 0.52 |
| stage 3 | RAC | 22 | GEA | 41 | 58 | 66 | 0.71 | 0.62 |
| | | | FMY | 61 | 58 | 58 | 1.05 | 1.05 |
| | | 27 | GEA | 43 | 58 | 66 | 0.74 | 0.65 |
| | | | FMY | 56 | 58 | 58 | 0.97 | 0.97 |
| | | 18 | GEA | 41 | 58 | 66 | 0.71 | 0.62 |
| | | | FMY | 60 | 58 | 58 | 1.03 | 1.03 |
| | RJT | 20 | KJC | 63 | 55 | 65 | 1.15 | 0.97 |
| | | | KAD | 55 | 64 | 24 | 0.86 | 2.29 |
| | | 24 | KJC | 66 | 55 | 65 | 1.20 | 1.02 |
| | | | KAD | 52 | 64 | 24 | 0.81 | 2.17 |
| stage 4 | JXG | 2 | FMY | 3 | 55 | 58 | 0.05 | 0.05 |
| | | 0 | PMR | 2 | 19 | 54 | 0.11 | 0.04 |
| | SRP | 5 | CKO | 5 | 19 | 60 | 0.26 | 0.03 |

[1]E:T ratio for arming assays is 100:1
[2]E:T ratio for NK assays is 50:1

TABLE 6

Serum ADCC against gp120-coated and HIV-infected targets (normal effectors)[1]

| | patient | CMC | gp120 ADCC | HIV ADCC | gp120 pt/pool | HIV pt/pool |
|---|---|---|---|---|---|---|
| stage 1 | DEK | 2 | 37 | 44 | 0.74 | 0.62 |
| | GPG | 8 | 22 | 66 | 0.53 | 0.93 |
| stage 2 | DBN | 55 | 46 | — | 1.05 | — |
| | JLG | 30 | 47 | 56 | 0.82 | 0.79 |
| stage 3 | RAC | 18 | 28 | — | 0.59 | — |
| | RJT | 20 | 12 | — | 0.28 | — | serum arming, also had persistently low CMC activity, and remarkable stability of both CD4% and absolute CD4 cell numbers (Table 3), related to extremely low ADCC against gp120-coated cells.

EXAMPLE 12

Effector ADCC and Arming Against $gp120_{IIIB}$-coated and $HIV_{IIIB}$-infected Targets Effector ADCC assays were performed in these patients to evaluate the relative contribution of ADCC-specific NK function to overall CMC activity in each of the proposed stages of the model (Table 7). Effector cell arming of low CMC individuals in stage 1 (DEK) and stage 4 (JXG) was also performed; effectors from individuals with high CMC are already armed with immune complexes and demonstrated high levels of lysis of gp120-adsorbed or HIV-infected target cells, in the absence of added antibody; the "no antibody" control against gp120-adsorbed or HIV-infected targets for ADCC assays was also high in individuals with high CMC. In Table 7, env-specific lysis was calculated as:

env-specific ADCC=[ADCC$_{(AB)}$]gp120/CEM.NK$^R$ − [ADCC$_{(AB)}$]CEM.NK$^R$ env-specific arming=[arming$_{(AB)}$]gp120/CEM.NK$^R$ − [arming$_{(AB)}$]CEM.NK$^R$ Individuals in stage 1 demonstrated reduced ability of NK cells to lyse gp120-coated targets, by CMC, by indirect ADCC (even in the presence of pool antibodies) or after arming with pool antibodies. Effector cell lysis of HIV-infected cells in the CMC and indirect ADCC assay was high in these same patients. This shows that other antibodies (in immune complexes), specifically directed to gp120 or gp41 on the surface of infected cells, were bound by NK cells from these individuals; these antibodies may not be replaced by pool antibodies during the arming assay incubation with undiluted pool sera. This describes a favorable situation in vivo, in which infected, but not uninfected cells are lysed by ADCC.

Stages 2 and 3 were characterized by similar effector cell function against gp120-coated and HIV-infected targets; serum indirect ADCC-mediating antibodies were also present in both stages, and CMC activity was similar (see Table 3 for additional stage 3 patients). The two stages differ primarily in the magnitude of circulating viral load and rate of CD4% decline, i.e., effectors were armed in both stages but gp120-coated cells were absent in JLG, but present in RAC.

specific immune complexes. Viral load differences between group 1 and 2 were modest; although an absolute threshold for the development of CMC- and arming-mediating immune complexes was not determined, that threshold may be affected by the antibody specificity and affinity found in a given individual. Differences in afffinity of primary isolate gp120 for autologous antibody and for CD4 affected the ability of ADCC to lyse gp120-coated cells in vivo.

Specific effector cell defects present in stage 1 patients rendered them incapable of mediating ADCC lysis of gp120-coated cells. These defects, if intrinsic, describe the one characteristic of a long-term survivor according to the present invention. Stage 1 patient DEK, infected with HIV since at least 1985, showed stable CD4%, CD4 cell count and asymptomatic clinical course, in the absence of antiretroviral therapy, i.e. the clinically accepted definition of a long-term non-progressor. This individual also showed high CD4 percentage, ranging from 57% to 69% during follow-up of the past 4 years.

Stage 2 patients are characterized by strong immune responses against both gp120-coated and HIV-infected target cells. In vivo, these responses could be either beneficial (at low viral load) or immunopathogenic (at high viral load). In the patients studied here, however, viral load and viral burden were very low. Thus, the immune responses noted would be predominantly directed against a small number of HIV-infected cells and not against gp12-coated CD4 cells.

TABLE 7

Effector cell function as assessed by K562 lysis, phenotype, ADCC and arming

| Stage | Patient | Date | NK activity | CD3$^-$ CD16$^+$ CD56$^+$ | gp120 CMC | gp120 ADCC w/pool | gp120 arming w/pool | HIV CMC | HIV ADCC w/pool |
|---|---|---|---|---|---|---|---|---|---|
| 1 | DEK | 10/25/94 | 80 | 11 | 9 | — | 9 | — | — |
|   |     | 2/28/94  | 61 | 8  | 2 | 7 | 0 | — | 47 |
|   | GPG | 4/18/95  | 35 | 8  | 8 | 14 | — | 48 | 55 |
|   |     | 12/6/95  | 38 | 8  | 12 | 9 | — | 34 | 33 |
|   | MB  | 12/13/95 | 36 | 8  | 11 | 9 | — | 33 | 38 |
| 2 | JLG | 4/19/95  | 47 | 19 | 22 | 35 | — | 34 | 53 |
|   |     | 6/29/95  | 71 | 21 | 43 | 50 | — | 68 | 62 |
|   | DBN | 6/1/95   | 50 | 8  | 29 | 23 | — | 35 | 34 |
| 3 | RAC | 7/26/95  | 60 | 6  | 10 | 29 | — | 23 | 41 |
|   | MAP | 12/5/95  | 48 | 12 | 23 | — | — | 36 | 40 |
| 4 | JXG | 10/24/94 | 30 | 5  | 0 | 3 | 2 | — | — |
|   |     | 2/9/95   | 29 | 3  | 0 | 4 | 0 | — | 4 |
|   |     | 9/7/95   | 17 | 2  | −2 | 5 | — | 3 | 11 |
|   | WJB | 4/5/95   | 16 | 3  | 0 | 1 | — | 17 | 4 |

EXAMPLE 13

Long Term Non-progression and in vitro Measures of ADCC Activity

Patients with high and stable CD4% are placed in stages 1 and 2 by the model of the present invention. NK cell lysis of K562 cells in these patients high, serum antibodies mediated ADCC against gp120-coated and HIV-infected targets, and effector cells mediated high levels of ADCC against HIV-infected targets. Differences in CMC activity between these two groups was shown by the inability of serum from stage 1 patients to arm normal effector cells. This is consistent with a relative lack of circulating, gp120-

EXAMPLE 14

Rapid CD4% Decline

Individuals in stage 3 exhibited rapid declines in CD4%, in the presence of effector cells which mediate CMC and ADCC, and with high serum arming antibodies. The ability of serum antibodies, immune complexes and effector cells to mediate in vivo ADCC was similar between patients in stages 2 and 3. Differences in infected cell burden (as measured by DNA PCR) and viral load (as measured by RNA PCR) showed that even ADCC against infected cells contributed to a rapid CD4% decline. In addition, in vivo ADCC was directed against gp120-coated, uninfected cells. The net lysis of both infected and uninfected cells explains rapid CD4 cell destruction, out of proportion to the replicating cell burden alone.

CMC activity, effector ADCC activity and, in some cases, antibody quantity and/or quality, declined as CD4% decreased, and that this can contributed to the leveling off of a rapid decline in CD4. Profound and continued CD4 cell loss, as seen in patient MAP (a drop of 13.5 percentage points per year over the past 19 months) was found in individuals who continued to mediate ADCC against infected or gp120-coated cells, despite low CD4%. The last assays prior to the initiation of antiretroviral therapy demonstrated that cells in MAP mediated high K562 killing (41%) and CMC lysis (18%), at a time when his CD4% and absolute CD4 cell counts were very low (4% and 60 cells/mm$^3$, respectively). This finding demonstrates that the present invention is useful for determining counterindication administration of agents, such as IL-2 or IL-12 which function to increase ADCC activity, and would thus cause increased CD4 destruction. Such detrimental effects were seen during IL-2 therapy in patients with high viral loads (Kovacs J. A. et al., supra).

EXAMPLE 15

Relationship Evaluation Using Statistical Analysis and Modeling

Model: CMC=viral load +CD4%.

The relationship between CMC, viral load and CD4% is first assessed empirically using graphical techniques. We plot the CMC level versus viral load and CD4% separately in order to determine the shape of the function. This allows empirical investigation of existence of a threshold for viral load, or continuous relationship. In the next step the range of viral load and CD4% levels is divided into subgroupings within which the relationship with CMC is approximately linear. If a threshold exists for viral load, this is accommodated as a separate subgrouping. The linear relationship within each subgrouping is estimated. Next, nonlinear regression models are examined to develop a more parsimonious analysis that may combine some of the subgroupings and/or provide a better model fit. A piecewise linear model is effective in modeling the relationship between CMC, viral load and CD4% with two subgroupings (stage 1 versus all other stages).

The analysis accommodates nonlinear relationships as well. Within each subgrouping, standard regression analysis is applied, and models are assessed using goodness of fit testing and examination of residuals. Regression coefficients are estimated using least squares (linear model) or maximum likelihood (non-linear model). These coefficients determine the strength of the relationships of viral load and CD4% with CMC level, including the possibility of a threshold level for viral load. Relationships that are statistically significant, (i.e., p<0.05) and a model that fits the empiriral data indicate that a relationship exists. Although this analysis does not prove a causal relationship, the model is used to determine the effects of changes in viral load and/or CD4% on CMC level.

An analysis of this model suggested that mean CMC is dependent on both the logarithm of mean CD4% and mean log RNA PCR (p=0.03 and p=0.02, respectively). From this analysis, the standard deviation of $\epsilon$ in this model was found to be 11.2, and the parameter estimates were −4.3 for mean RNA PCR and 0.6 for mean CD4%. With a sample size of 60, and assuming that the estimates derived from the analysis approximate the actual population values, the statistical power becomes greater than 97% for detecting a relationship at least as strong as was observed in here (using the non-central F distribution with 2 and 57 degrees of freedom and α=0.05).

Alternative Model: rate of CD4% decline is correlated with CMC activity and viral load. The relationship between changes in CD4% over time and CMC and viral load is investigated in two ways. In the first analysis, an ordinary multiple regression model, looking at aggregated data from each patient is used. Three variables are computed for each patient 1) mean CMC activity, 2) mean viral load, and 3) the slope of the regression line predicting CD4% over time. A regression model is then estimated in which the change in CD4% per year (i.e., slope) is the dependent variable and mean CMC and viral load are the independent variables. This model will have the following form:

$$\Delta CD4\% = \alpha + \beta_1 \times CMC + \beta_2 \times VL + \epsilon,$$

where $\Delta CD4\%$ denotes the slope of CD4 over time, CMC denotes the mean CMC activity, VL denoted the mean viral load, α and β1 and β2 are unknown regression parameters, and $\epsilon$ is a normally distributed error term. Statistical power for this model is similar to that for the first model above.

In the second analysis, a repeated measures model which does not require aggregated patient data is used. This model predicts the change in CD4% between each measurement in time. At each time the assays are conducted, the change in CD4% since the previous assay is computed as well as the time duration between the assays. The model for this analysis has the form:

$$\Delta CD4\%_j = \alpha + \beta_{1j} \times CMC_j + \beta_{2j} \times VL - \epsilon_j,$$

where $\Delta CD4\%_j$ is the change in CD4% from the $(j-1)^{st}$ assay to the $j^{th}$ assay, CMC is the CMC level at the $j^{th}$ assay, $\beta_{1j}$ is the viral load level at the $j^{th}$ assay, α $\beta_{1j}$ and $\beta_{1j}$ are unknown regression coefficients, and $\epsilon_j$ is a normally distributed error term. The subscript j ranges from 1 to the total number of assays for each patient. The error terms associated with each individual are assumed to have a multivariate normal distribution with zero mean vector and unknown covariance matrix. If the time duration between assays is approximately equal from patient to patient, no assumptions are made to the form of the covariance matrix. In this case, the observed data are used to estimate the covariance matrix. On the other hand, if there are large discrepancies in the time durations between assays from patient to patient (i.e., a range of two months), we will take this into consideration using a spatial form (such as an AR(1) model) for the covariance matrix. In either case, standard software can be used to estimate the regression parameters. (PROC MIXED in SAS, SAS Institute, Inc.).

This second model provides a more complete analysis of the relationships of changes in CD4%, viral load and CMC activity over time. If the two analyses provide very similar results, we focus on the first analysis. We conclude that a relationship exists with statistically significant (P<0.05) regression parameters, and the model fits the data. Also, this model provides the statistical basis for estimating effects of changes in viral load and CMC on CD4%.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method for prognosticating the onset of disease in a subject with a retrovirus infection, comprising:

obtaining a biological sample from the subject;

contacting said sample with target cells, wherein said target cells are uninfected with the retrovirus, and wherein said target cells have been coated with a viral protein;

determining the % cell mediated cytotoxicity (CMC) lysis in the sample;

determining retroviral load in the subject; and predicting the rate of CD4% decline as a function of the interaction of the % CMC lysis and viral load;

to thereby prognosticate the onset of disease in said subject.

2. The method of claim 1, in which the viral protein is an envelope protein.

3. The method of claim 1, in which the viral protein coats the target cells in vitro.

4. The method of claim 1, in which the interaction of the % CMC lysis and viral load is determined by multiplying the % CMC lysis and the logarithm of the viral load.

5. The method of claim 1, in which the subject is infected with a virus selected from the group consisting of HIV-1, HIV-2, BIV, SIV, and FELV.

6. The method of claim 5, in which the virus is HIV-1 or HIV-2.

7. The method of claim 6, in which the cell mediated toxicity is determined using an assay with $CD4^+$ cell line target cells.

8. The method of claim 7, in which the cell mediated toxicity assay measures indirect antibody-dependent cellular-cytotoxicity lysis of gp120-absorbed $CEM.NK^R$ target cells by normal effector cells, said effector and said $CD4^+$ cell line target cells being supplied in vitro with serum from said HIV infected patient.

9. The method of claim 1, in which retroviral load is determined by assay of gag gene product.

10. The method of claim 9, in which assay of gag gene product is by PCR analysis.

11. The method of claim 10, in which the PCR assay of gag gene product is by RNA PCR analysis.

12. The method of claim 6 in which progression of said HIV infection is diagnosed according to one of four sequential post-seroconversion stages, wherein the first stage is characterized by antibody excess, the second stage is characterized by low levels of immune complexes, the third stage is characterized by antigen excess, and the fourth stage is characterized by effector cell dysfunction.

13. The method of claim 1, in which the retroviral load is determined by PCR.

14. The method of claim 13, in which the PCR is RNA PCR (RT PCR).

15. The method of claim 8, in which serum is further incubated and centrifuged to obtain plasma prior to assay.

16. A kit for prognosticating the onset of disease in a subject with a retrovirus infection, comprising reagents for RNA PCR, reagents for cell-mediated cytotoxicity assay, apparatus for obtaining blood samples from said subject, a container, and instructions for use.

17. The method of claim 6, in which the subject has greater than 400 CD4 cells/$mm^3$ in said biological sample.

18. The method of claim 1, wherein said disease is AIDS.

19. A method for predicting the rate of CD4% decline in a subject with a retrovirus infection, comprising:

obtaining a biological sample from the subject;

contacting said sample with target cells, wherein said target cells are uninfected with the retrovirus, and wherein said target cells have been coated with a viral protein;

determining the % cell mediated cytotoxicity (CMC) lysis in the sample;

determining retroviral load in the subject; and determining the interaction of the % CMC lysis and viral load; to thereby prognosticate the onset of disease in said subject.

* * * * *